US009333202B2

(12) United States Patent
Petrukhin et al.

(10) Patent No.: US 9,333,202 B2
(45) Date of Patent: May 10, 2016

(54) NON-RETINOID ANTAGONISTS FOR TREATMENT OF AGE-RELATED MACULAR DEGENERATION AND STARGARDT DISEASE

(71) Applicants: Konstantin Petrukhin, New Windsor, NY (US); Janet R. Sparrow, New York, NY (US); Rando Allikmets, Cornwall on Hudson, NY (US)

(72) Inventors: Konstantin Petrukhin, New Windsor, NY (US); Janet R. Sparrow, New York, NY (US); Rando Allikmets, Cornwall on Hudson, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/398,342

(22) PCT Filed: Apr. 30, 2013

(86) PCT No.: PCT/US2013/038905
§ 371 (c)(1),
(2) Date: Oct. 31, 2014

(87) PCT Pub. No.: WO2013/166037
PCT Pub. Date: Nov. 7, 2013

(65) Prior Publication Data
US 2015/0126494 A1    May 7, 2015

Related U.S. Application Data

(60) Provisional application No. 61/641,106, filed on May 1, 2012.

(51) Int. Cl.
| | |
|---|---|
| *A61K 31/55* | (2006.01) |
| *A61K 31/497* | (2006.01) |
| *A61K 31/496* | (2006.01) |
| *A61K 31/451* | (2006.01) |
| *A61K 31/4525* | (2006.01) |
| *A61K 31/454* | (2006.01) |
| *A61K 31/4545* | (2006.01) |
| *A61K 31/495* | (2006.01) |
| *A61K 31/506* | (2006.01) |
| *A61K 31/519* | (2006.01) |
| *A61K 31/551* | (2006.01) |

(52) U.S. Cl.
CPC ............ *A61K 31/496* (2013.01); *A61K 31/451* (2013.01); *A61K 31/454* (2013.01); *A61K 31/4525* (2013.01); *A61K 31/4545* (2013.01); *A61K 31/495* (2013.01); *A61K 31/506* (2013.01); *A61K 31/519* (2013.01); *A61K 31/551* (2013.01)

(58) Field of Classification Search
CPC ... C07D 401/12; A61K 31/495; A61K 31/505
USPC ................................. 514/218, 252.1, 252.14
See application file for complete search history.

(56) References Cited

U.S. PATENT DOCUMENTS

| | | |
|---|---|---|
| 5,231,083 A | 7/1993 | Linz et al. |
| 5,312,814 A | 5/1994 | Biller et al. |
| 5,523,430 A | 6/1996 | Patel et al. |
| 5,532,243 A | 7/1996 | Gilligan et al. |
| 5,703,091 A | 12/1997 | Steiner et al. |
| 6,372,793 B1 | 4/2002 | Lamango et al. |
| 6,638,980 B1 | 10/2003 | Su et al. |
| 7,157,451 B2 | 1/2007 | Atwal et al. |
| 7,501,405 B2 | 3/2009 | Kampen et al. |
| 7,718,669 B2 | 5/2010 | Petry et al. |
| 7,781,436 B2 | 8/2010 | Bissantz et al. |
| 8,168,783 B2 | 5/2012 | Kokubo et al. |
| 8,980,924 B2 | 3/2015 | Petrukhin et al. |
| 2003/0195195 A1 | 10/2003 | Haviv et al. |
| 2004/0097575 A1 | 5/2004 | Doherty et al. |
| 2004/0180877 A1 | 9/2004 | Peters et al. |
| 2004/0220171 A1 | 11/2004 | Pauls et al. |
| 2006/0074121 A1 | 4/2006 | Chen et al. |
| 2006/0089378 A1 | 4/2006 | Xia et al. |
| 2006/0111366 A1 | 5/2006 | Anderson et al. |
| 2006/0135460 A1 | 6/2006 | Widder et al. |
| 2006/0199837 A1 | 9/2006 | Thompson et al. |
| 2006/0270688 A1 | 11/2006 | Chong et al. |
| 2007/0015827 A1 | 1/2007 | Widder et al. |
| 2007/0254911 A1 | 11/2007 | Xia et al. |
| 2008/0039442 A1 | 2/2008 | Blom et al. |
| 2008/0051409 A1 | 2/2008 | Gmeiner et al. |

(Continued)

FOREIGN PATENT DOCUMENTS

| | | |
|---|---|---|
| DE | 4130514 | 3/1993 |
| EP | 1190710 A1 | 3/2002 |

(Continued)

OTHER PUBLICATIONS

Motani, A. et al. (2009). Identification and characterization of a non-retinoid ligand for retinol-binding protein 4 which lowers serum retinol-binding protein 4 levels in vivo. *The Journal of Biological Chemistry*, 284(12), 7673-7680.

(Continued)

*Primary Examiner* — Raymond Henley, III
(74) *Attorney, Agent, or Firm* — John P. White; Cooper & Dunham LLP

(57) ABSTRACT

A method for treating a disease characterized by excessive lipofuscin accumulation in the retina in mammals afflicted therewith, comprising administering to the mammal an effective amount of a non-retinoid antagonist compound or a pharmaceutically acceptable salt thereof.

15 Claims, 21 Drawing Sheets

(56) References Cited

U.S. PATENT DOCUMENTS

| | | |
|---|---|---|
| 2008/0139552 A1 | 6/2008 | Bissantzet et al. |
| 2008/0254140 A1 | 10/2008 | Widder et al. |
| 2009/0054532 A1 | 2/2009 | Mata et al. |
| 2009/0082362 A1 | 3/2009 | Bakthavatchalam et al. |
| 2009/0088435 A1 | 4/2009 | Mata et al. |
| 2009/0143376 A1 | 6/2009 | Milburn et al. |
| 2010/0022530 A1 | 1/2010 | Schiemann et al. |
| 2010/0063047 A1 | 3/2010 | Borchardt et al. |
| 2010/0222357 A1 | 9/2010 | Bizzantz et al. |
| 2010/0292206 A1 | 11/2010 | Kasai et al. |
| 2011/0003820 A1 | 1/2011 | Henrich et al. |
| 2011/0201657 A1 | 8/2011 | Boueres et al. |
| 2011/0251182 A1 | 10/2011 | Sun et al. |
| 2011/0251187 A1 | 10/2011 | Kasai et al. |
| 2011/0257196 A1 | 10/2011 | Lu et al. |
| 2011/0319393 A1 | 12/2011 | Chassaing et al. |
| 2011/0319412 A1 | 12/2011 | Sakagami et al. |
| 2012/0010186 A1 | 1/2012 | Lachance et al. |
| 2012/0065189 A1 | 3/2012 | Takahashi et al. |
| 2012/0071489 A1 | 3/2012 | Kasai et al. |
| 2012/0071503 A1 | 3/2012 | Cosford et al. |
| 2012/0077844 A1 | 3/2012 | Cavezza et al. |
| 2012/0077854 A1 | 3/2012 | Petrassi et al. |
| 2014/0031392 A1 | 1/2014 | Petrukhin et al. |
| 2015/0057320 A1 | 2/2015 | Petrukhin et al. |
| 2015/0315197 A1 | 11/2015 | Petrukhin et al. |

FOREIGN PATENT DOCUMENTS

| | | |
|---|---|---|
| JP | 2006-0770063 | 3/2006 |
| JP | 2006-176503 | 7/2006 |
| WO | WO 97/17954 | 5/1997 |
| WO | WO 97/38665 | 10/1997 |
| WO | WO 98/39000 | 9/1998 |
| WO | WO 99/37304 | 7/1999 |
| WO | WO 99/65867 | 12/1999 |
| WO | WO 00/21557 | 4/2000 |
| WO | WO 00/42852 | 7/2000 |
| WO | WO 00/61606 | 10/2000 |
| WO | WO 01/07436 | 2/2001 |
| WO | WO 2011/059881 A1 | 5/2001 |
| WO | WO 01/66114 A1 | 9/2001 |
| WO | WO 01/87921 A2 | 11/2001 |
| WO | WO 02/05819 A1 | 1/2002 |
| WO | WO 03/024450 A1 | 3/2003 |
| WO | WO 03/024456 A1 | 3/2003 |
| WO | WO 03/032914 A2 | 4/2003 |
| WO | WO 03/066581 A1 | 8/2003 |
| WO | WO 03/076400 A1 | 9/2003 |
| WO | WO 2004/002531 A1 | 1/2004 |
| WO | WO 2004/010942 A2 | 2/2004 |
| WO | WO 2004/014374 A1 | 2/2004 |
| WO | WO 2004/017950 A2 | 3/2004 |
| WO | WO 2004/034963 A2 | 4/2004 |
| WO | WO 2005/074535 A3 | 8/2005 |
| WO | WO 2005/087226 A1 | 9/2005 |
| WO | WO 2006/003030 A1 | 1/2006 |
| WO | WO 2006/004201 | 1/2006 |
| WO | WO 2006/034441 A1 | 3/2006 |
| WO | WO 2006/034446 A1 | 3/2006 |
| WO | WO 2006/049880 A1 | 5/2006 |
| WO | WO 2006/065479 A2 | 6/2006 |
| WO | WO 2006/085108 A1 | 8/2006 |
| WO | WO 03/092606 A2 | 11/2006 |
| WO | WO 2006/138657 A1 | 12/2006 |
| WO | WO 2007/020888 A1 | 2/2007 |
| WO | WO 2007/027532 A2 | 3/2007 |
| WO | WO 2007/037187 A1 | 4/2007 |
| WO | WO 2007/086584 A1 | 8/2007 |
| WO | WO 2008/045393 A2 | 4/2008 |
| WO | WO 2009/023179 A2 | 2/2009 |
| WO | WO 2009/042444 A2 | 4/2009 |
| WO | WO 2009/051244 | 4/2009 |
| WO | WO 2010/077915 A1 | 7/2010 |
| WO | WO 2010/088050 A2 | 8/2010 |
| WO | WO 2010/091409 A1 | 8/2010 |
| WO | WO 2010/119992 A1 | 10/2010 |
| WO | WO 2010/120741 A1 | 10/2010 |
| WO | WO 2011/156632 A2 | 12/2011 |
| WO | WO 2012/025164 A1 | 3/2012 |
| WO | WO 2012/071369 A2 | 5/2012 |
| WO | WO 2012/158844 A1 | 11/2012 |
| WO | WO 2013/166037 A1 | 11/2013 |
| WO | WO 2013/166040 A1 | 11/2013 |
| WO | WO 2013/166041 A1 | 11/2013 |
| WO | WO 2014/151936 A1 | 9/2014 |
| WO | WO 2014/151959 A1 | 9/2014 |
| WO | WO/2014/152013 A1 | 9/2014 |
| WO | WO 2014/152018 A1 | 9/2014 |
| WO | WO 2014/160409 A1 | 10/2014 |
| WO | WO 2004/108135 A1 | 12/2014 |
| WO | WO 2015/168286 A1 | 11/2015 |

OTHER PUBLICATIONS

Notification of Transmittal of the International Search Report and the Written Opinion of the International Searching Authority, or the Declaration, including an International Search Report and Written Opinion of the International Searching Authority, mailed Sep. 27, 2013 in connection with PCT International Application No. PCT/US2013/038905, filed Apr. 30, 2013.

International Search Report in connection with PCT/US2011/061763 issued May 29, 2012.

International Preliminary Report on Patentability in connection with PCT/US2011/061763 issued May 29, 2012.

Written Opinion issued May 29, 2012 in connection with PCT/US2011/061763.

Notification of Transmittal of the International Search Report and the Written Opinion of the International Searching Authority, or the Declaration issued May 29, 2012 in connection with PCT/US2011/061763.

Office Action issued Apr. 10, 2014 in connection with U.S. Appl. No. 13/988,754.

Notice of Allowance issued Feb. 10, 2015 in connection with U.S. Appl. No. 13/988,754.

Extended European Search Report issued Aug. 19, 2014 in connection with European Patent Application No. 11842785.5.

Office Action (including English Language summary thereof prepared by Japanese agent) issued Sep. 29, 2015 in connection with Japanese Patent application No. 2013-541006.

International Search Report in connection with PCT/US2013/038908 issued Sep. 20, 2013.

International Preliminary Report on Patentability in connection with PCT/US2013/038908 issued Nov. 4, 2014.

Written Opinion issued Sep. 20, 2013 in connection with PCT/US2013/038908.

Notification of Transmittal of the International Search Report and the Written Opinion of the International Searching Authority, or the Declaration issued Sep. 20, 2013 in connection with PCT/US2013/038908.

International Search Report in connection with PCT/US2013/038905 issued Sep. 27, 2013.

International Preliminary Report on Patentability in connection with PCT/US2013/038905 issued Nov. 4, 2014.

Written Opinion issued Sep. 24, 2013 in connection with PCT/US2013/038905 issued Sep. 24, 2013.

International Search Report in connection with PCT/US2013/038910 issued Sep. 24, 2013.

International Preliminary Report on Patentability in connection with PCT/US2013/038910 issued Nov. 4, 2014.

Written Opinion issued Sep. 24, 2013 in connection with PCT/US2013/038910.

Notification of Transmittal of the International Search Report and the Written Opinion of the International Searching Authority, or the Declaration issued Sep. 24, 2013 in connection with PCT/US2013/038910.

International Search Report in connection with PCT/US2014/026813 issued Jul. 18, 2014.

(56) References Cited

OTHER PUBLICATIONS

International Preliminary Report on Patentability in connection with PCT/US2014/026813 issued Sep. 15, 2015.
Written Opinion of the International Searching Authority issued Jul. 18, 2014 in connection with PCT/US2014/026813.
Notification of Transmittal of the International Search Report and the Written Opinion of the International Searching Authority, or the Declaration issued Jul. 18, 2014 in connection with PCT/US2014/026813.
International Search Report in connection with PCT/US2014/026523 issued Aug. 22, 2014.
International Preliminary Report on Patentability in connection with PCT/US2014/026523 issued Sep. 15, 2015.
Written Opinion issued Aug. 22, 2014 in connection with PCT/US2014/026523.
Notification of Transmittal of the International Search Report and the Written Opinion of the International Searching Authority, or the Declaration issued Aug. 22, 2014 in connection with PCT/US2014/026818 issued Aug. 22, 2014 in connection with PCT/US2014/026523.
International Search Report in connection with PCT/US2014/026818 issued Jul. 18, 2014.
International Preliminary Report on Patentability in connection with PCT/US2014/026818 issued Sep. 15, 2015.
Written Opinion issued Jul. 18, 2014 in connection with PCT/US2014/026818.
Notification of Transmittal of the International Search Report and the Written Opinion of the International Searching Authority, or the Declaration issued Jul. 18, 2014 in connection with PCT/US2014/026818.
International Search Report in connection with PCT/US2014/026730 issued Jul. 21, 2014.
International Preliminary Report on Patentability in connection with PCT/US2014/026730 issued Sep. 15, 2015.
Written Opinion issued Jul. 21, 2014 in connection with PCT/US2014/026730.
Notification of Transmittal of the International Search Report and the Written Opinion of the International Searching Authority, or the Declaration issued Jul. 21, 2014 in connection with PCT/US2014/026730.
International Search Report in connection with PCT/US2014/026699 issued Jul. 18, 2014.
International Preliminary Report on Patentability in connection with PCT/US2014/026699 issued Sep. 15, 2015.
Written Opinion of the International Searching Authority in connection with PCT/US2014/026699 issued Jul. 18, 2014.
Notification of Transmittal of the International Search Report and the Written Opinion of the International Searching Authority, or the Declaration issued Jul. 18, 2014 in connection with PCT/US2014/026699.
International Search Report in connection with PCT/US2015/028293 issued Jul. 10, 2015.
Written Opinion issued Jul. 10, 2015 in connection with PCT/US2015/028293.
Notification of Transmittal of the International Search Report and the Written Opinion of the International Searching Authority, or the Declaration issued May 11, 2015 in connection with PCT/US2015/028293.
Office Action issued Nov. 25, 2015 in connection with U.S. Appl. No. 14/699,672.
Petrukhin (2007) New therapeutic targets in atrophic age-related macular degeneration. Expert Opin Ther Targets. 11(5):625-639; p. 629.
Sparrow, et al. (2010) Phospholipid meets all-trans-retinal: the making of RPE bisretinoids. Lipid Res 51(2): 247-261.
Elenewski, at al (2010) Free energy landscape of the retinol/serum retinol binding protein complex: a biological host-guest system. J Phys Chem B 02, 114(34):11315-11322.
Sharif et al (2009) Time resolved fluorescence resonance energy transfer and surface plasmon resonance-based assays for retinoid and transthyretin binding to retinol-binding protein 4. Anal Biochem, 392(2):162-168.
Bourgault, S. et al. (2011) Mechanisms of transthyretin cardiomyocyte toxicity inhibition by resveratrol analogs. Biochem Biophys Res Commun. 410(4):707-13.
Wu et al (2009) Novel Lipofuscin bisretinoids prominent in human retina and in a model of recessive Stragardt disease. J. Biol. Chem. 284(30) 20155-20166.
Sparrow, et al. (2010) Interpretations of Fundus Autofluorescence from Studies of the Bisretinoids of the Retina. Invest. Ophthalmol. Vis. Sci. vol. 51 No. 9 4351-4357.
Dobri et al (2013) A1120, a Nonretinoid RBP4 Antagonist, Inhibits Formation of Cytotoxic Bisretinoids in the Animal Model of Enhanced Retinal Lipofuscinogenesis. Investigative Ophthalmology & Visual Science, vol. 54, No. 1, 85-95.
Nov. 8, 2010 CAS Search Report.
Feb. 24, 2013 CAS Search Report.
Mar. 5, 2013 CAS Search Report.
Dec. 9, 2014 CAS Search Report.
Office Action issued Dec. 10, 2015 in connection with U.S. Appl. No. 14/530,516.

NON-RETINOID ANTAGONISTS FOR TREATMENT OF AGE-RELATED MACULAR DEGENERATION AND STARGARDT DISEASE

CROSS-REFERENCE TO RELATED APPLICATIONS

This application is a §371 national stage of PCT International Application No. PCT/US2013/038905, filed Apr. 30, 2013, claiming the benefit of U.S. Provisional Application No. 61/641,106, filed May 1, 2012, the contents of each of which are hereby incorporated by reference in their entirety.

This invention was made with government support under grant number NS067594 awarded by National Institutes of Health. The government has certain rights in the invention.

Throughout this application, certain publications are referenced in parenthesis. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Age-related macular degeneration (AMD) is the leading cause of blindness in developed countries. It is estimated that 62.9 million individuals worldwide have the most prevalent atrophic (dry) form of AMD; 8 million of them are Americans. Due to increasing life expectancy and current demographics this number is expected to triple by 2020. There is currently no FDA-approved treatment for dry AMD. Given the lack of treatment and high prevalence, development of drugs for dry AMD is of upmost importance. Clinically, atrophic AMD represents a slowly progressing neurodegenerative disorder in which specialized neurons (rod and cone photoreceptors) die in the central part of the retina called macula (1). Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD (2-9). In addition to AMD, dramatic accumulation of lipofuscin is the hallmark of Stargardt Disease (STGD), an inherited form of juvenile-onset macular degeneration. The major cytotoxic component of RPE lipofuscin is pyridinium bisretinoid A2E (FIG. 1). Additional cytotoxic bisretinoids are isoA2E, atRAL di-PE, and A2-DHP-PE (40, 41). Formation of A2E and other lipofuscin bisretinoids, such as A2-DHP-PE (A2-dihydropyridine-phosphatidylethanolamine) and atRALdi-PE (all-trans-retinal dimer-phosphatidylethanolamine), begins in photoreceptor cells in a non-enzymatic manner and can be considered as a by-product of the properly functioning visual cycle.

A2E is a product of condensation of all-trans retinaldehyde with phosphatidyl-ethanolamine which occurs in the retina in a non-enzymatic manner and, as illustrated in FIG. 4, can be considered a by-product of a properly functioning visual cycle (10). Light-induced isomerization of 11-cis retinaldehyde to its all-trans form is the first step in a signaling cascade that mediates light perception. The visual cycle is a chain of biochemical reactions that regenerate visual pigment (11-cis retinaldehyde conjugated to opsin) following exposure to light.

As cytotoxic bisretinoids are formed during the course of a normally functioning visual cycle, partial pharmacological inhibition of the visual cycle may represent a treatment strategy for dry AMD and other disorders characterized by excessive accumulation of lipofuscin (25-27, 40, 41).

SUMMARY OF THE INVENTION

The present invention relates to a method for treating a disease characterized by excessive lipofuscin accumulation in the retina in mammal afflicted therewith, comprising administering to the mammal an effective amount of a compound having the structure:

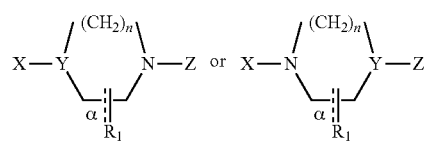

wherein
n=2 or 3;
$R_1$ is absent or present and when present, is $CH_3$ or O;
α is absent or present,
   wherein when α present, then $R_1$ is O, and when α ia absent, then $R_1$ is $CH_3$;
X is

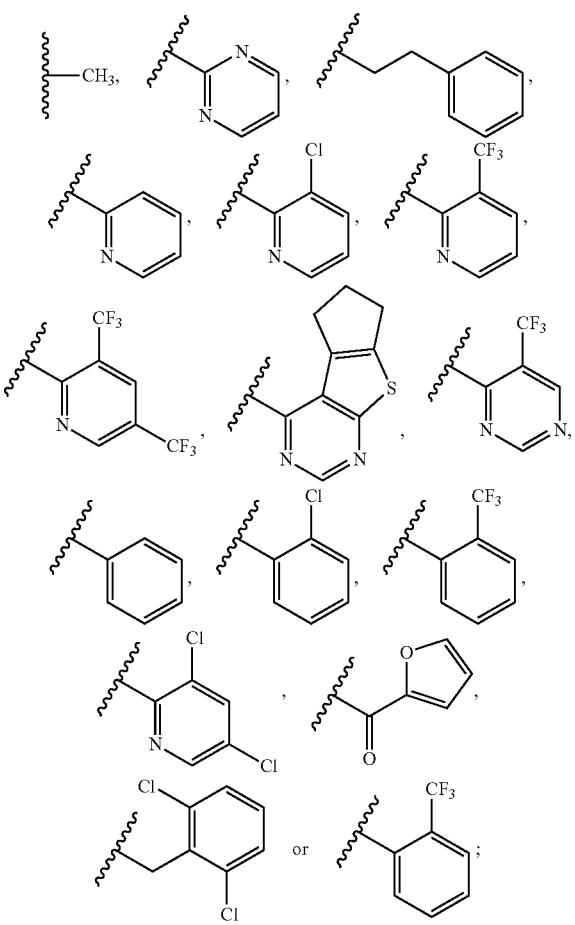

Y is N or C;

Z is
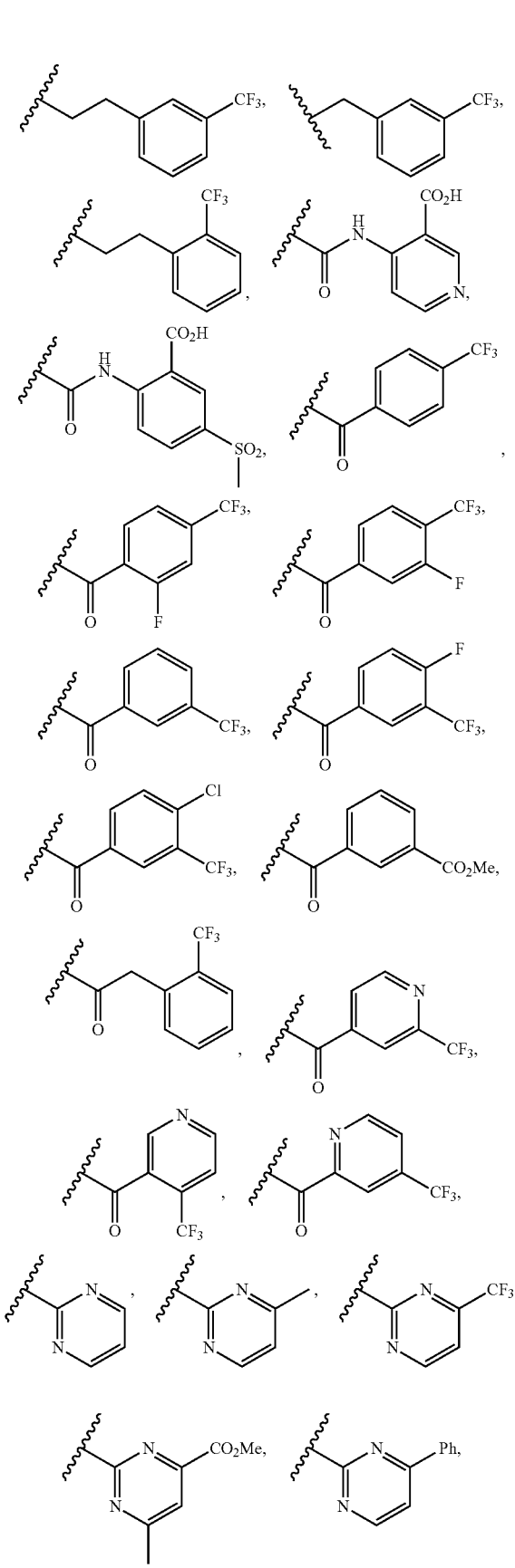
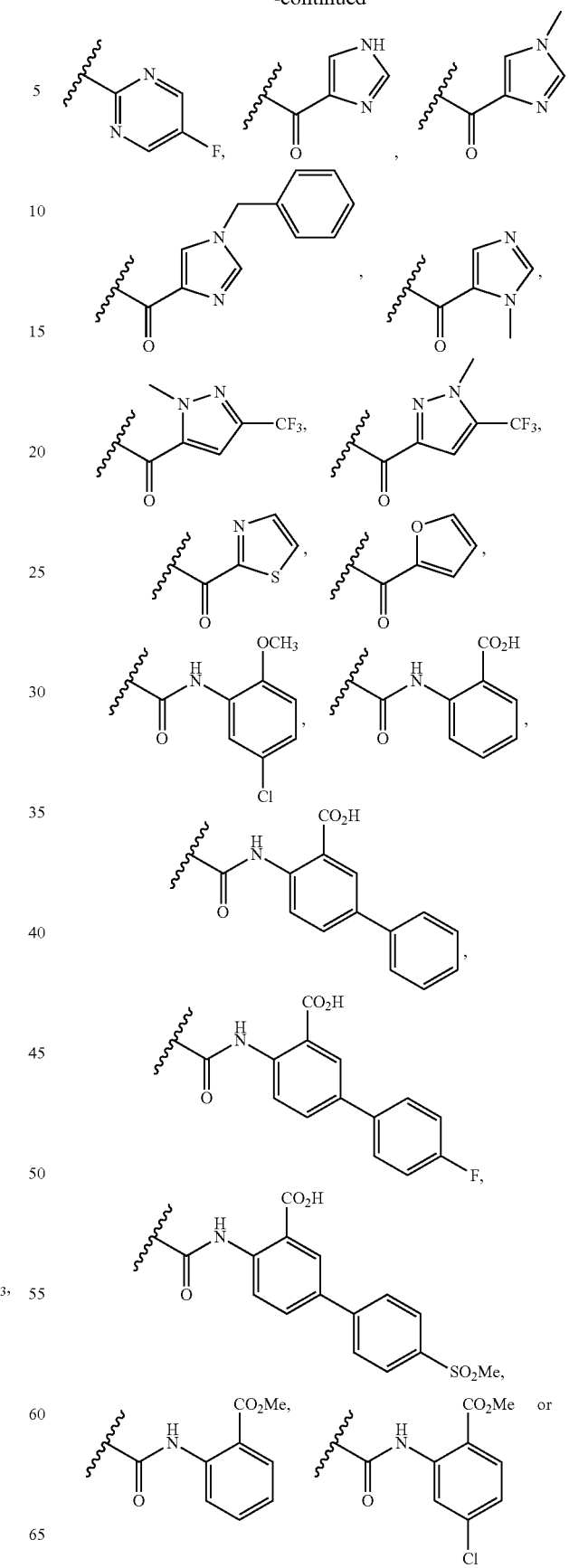

-continued

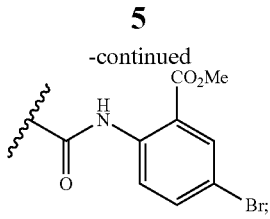

and
when n=2, R₁ is absent, X is

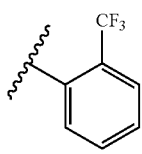 [SMILES: *c1ccccc1C(F)(F)F]

and Y is C,
then Z is other than

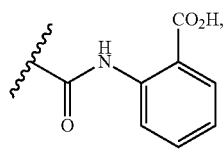

or a pharmaceutically acceptable salt thereof.

BRIEF DESCRIPTION OF THE FIGURES

FIG. 14. SPA Binding Assay for RBP4 and HTRF Assay for Antagonists of RBP4-TTR Interaction.

DETAILED DESCRIPTION OF THE INVENTION

Figure 1:
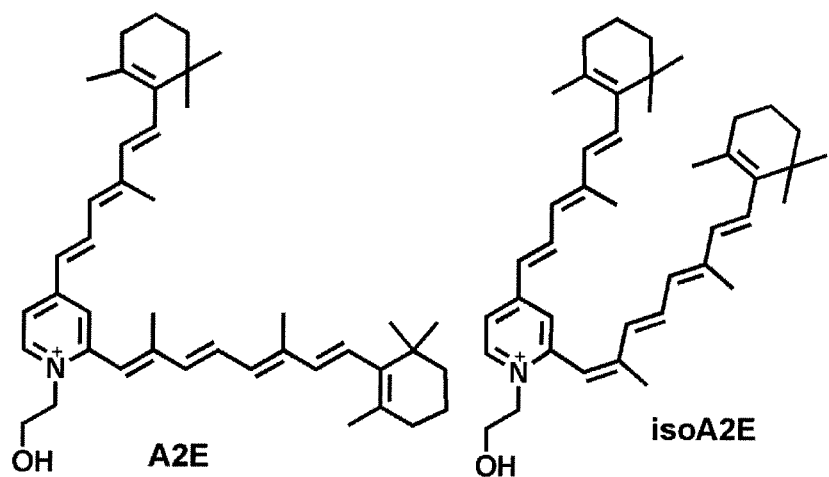
FIG. 1. Structure of bisretinoid A2E, a cytotoxic component of retinal lipofuscin.

The present invention relates to a method for treating a disease characterized by excessive lipofuscin accumulation in the retina in mammal afflicted therewith, comprising administering to the mammal an effective amount of a compound having the structure:

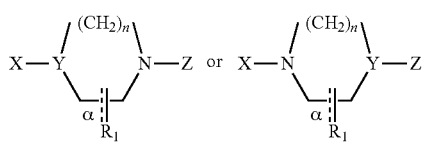
wherein
n=2 or 3;
R₁ is absent or present and when present, is CH₃ or O;
α is absent or present,
 wherein when α present, then R₁ is O, and when α is absent, then R₁ is CH₃;
X is
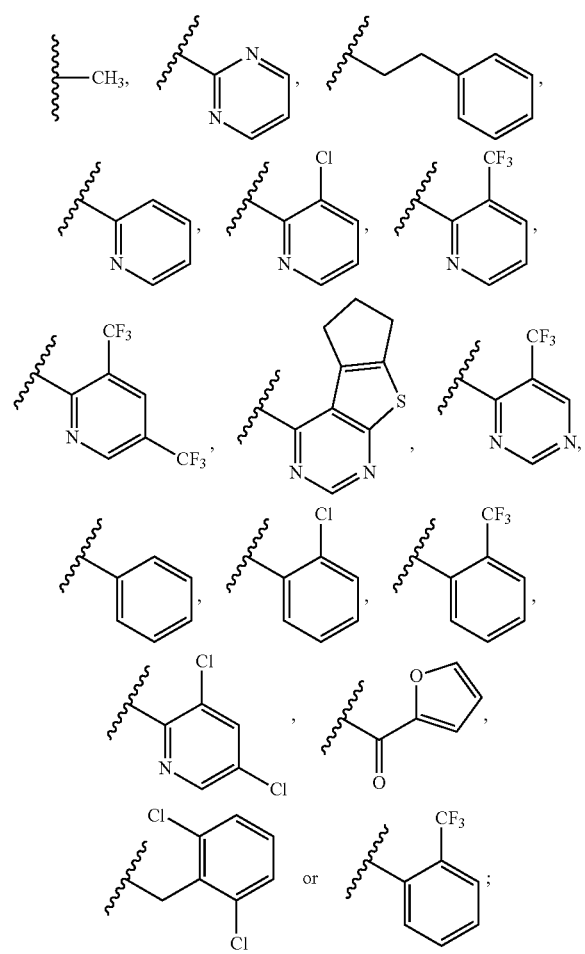
Y is N or C;
Z is
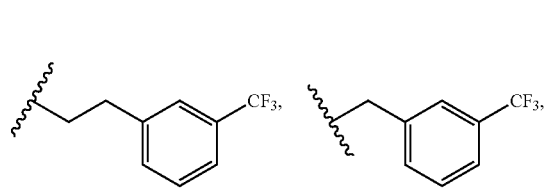
-continued
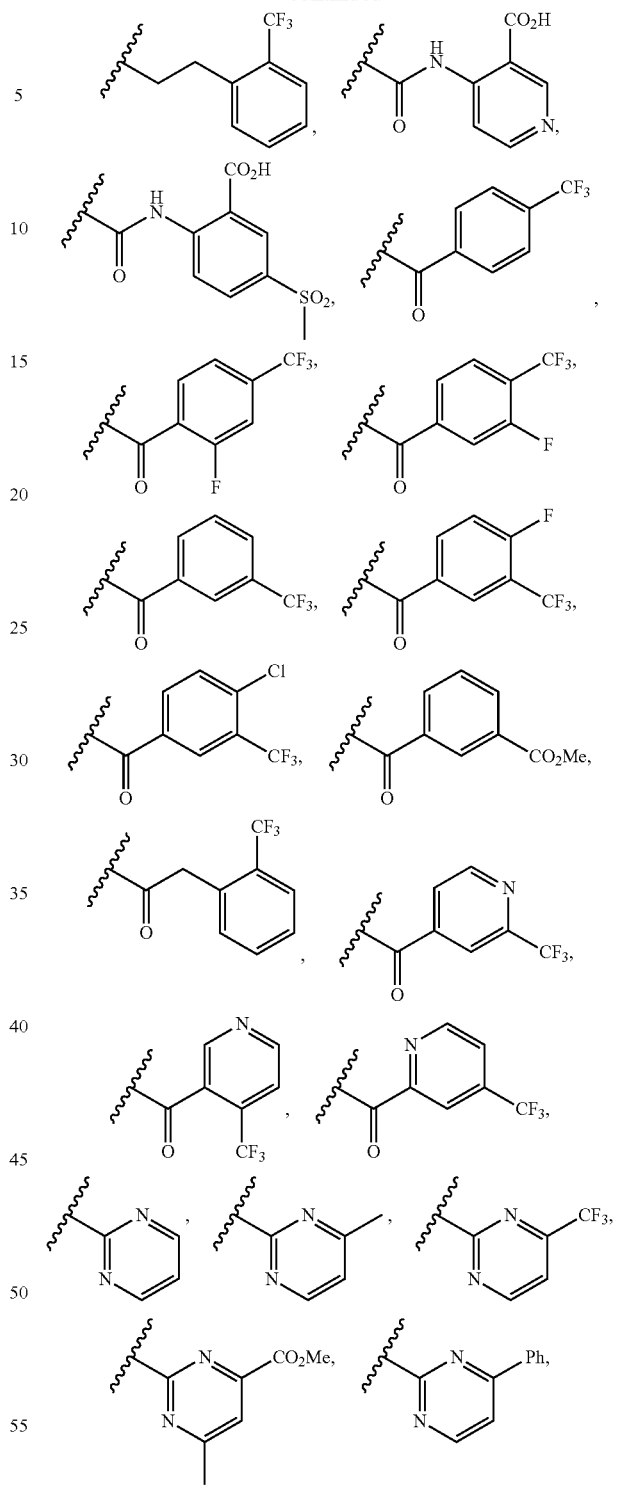
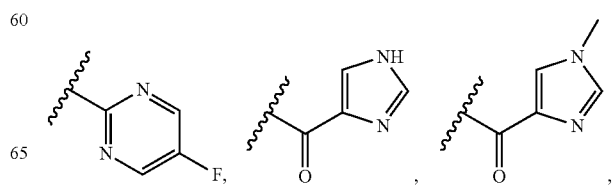

-continued
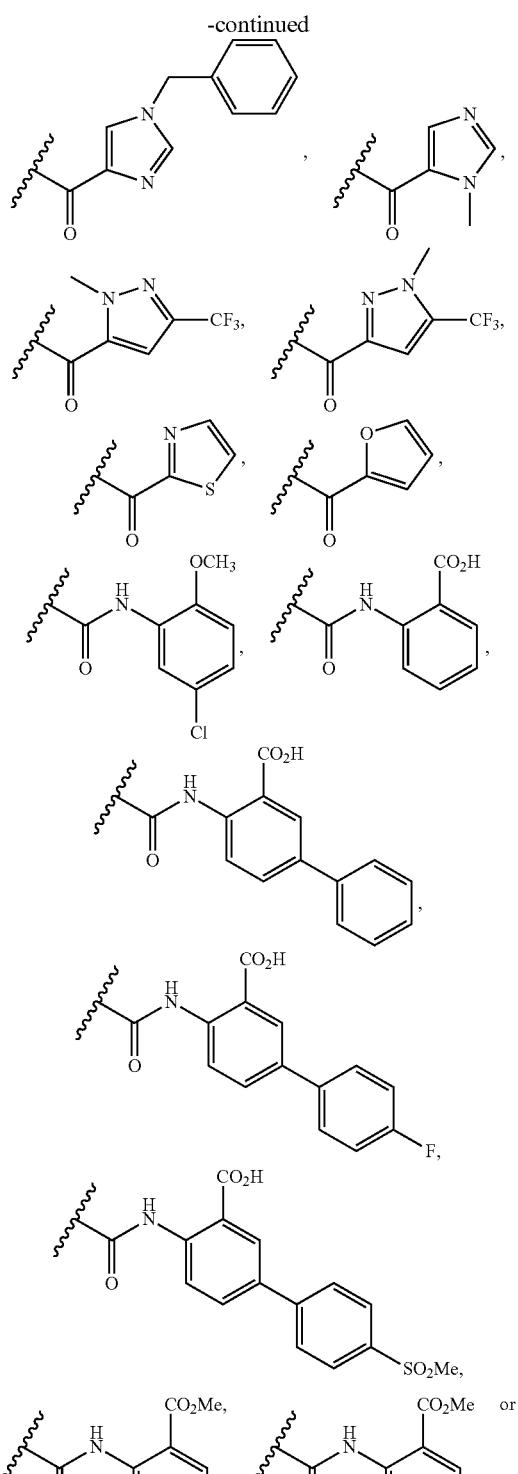
and
when n=2, $R_1$ is absent, X is
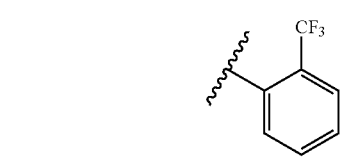
and Y is C,
then Z is other than
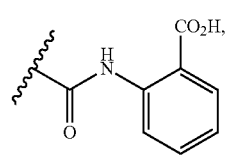 [SMILES: *C(=O)Nc1ccccc1C(=O)O]
or a pharmaceutically acceptable salt thereof.
In some embodiments, the compound has the structure
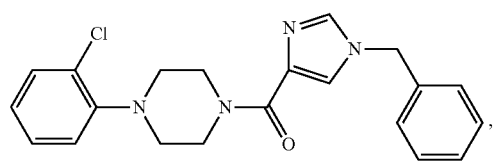
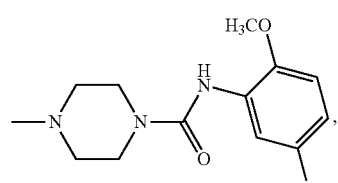
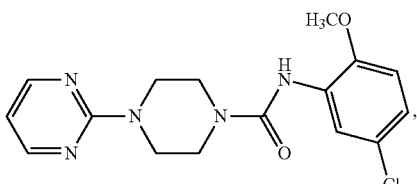
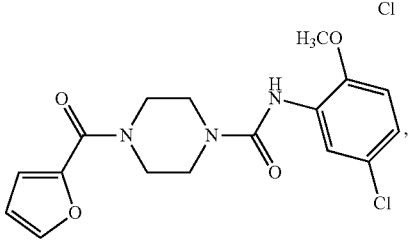
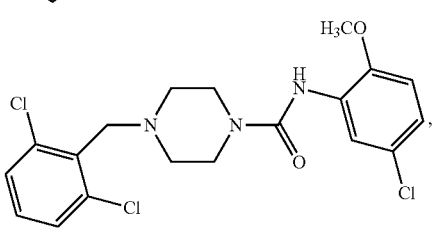

-continued
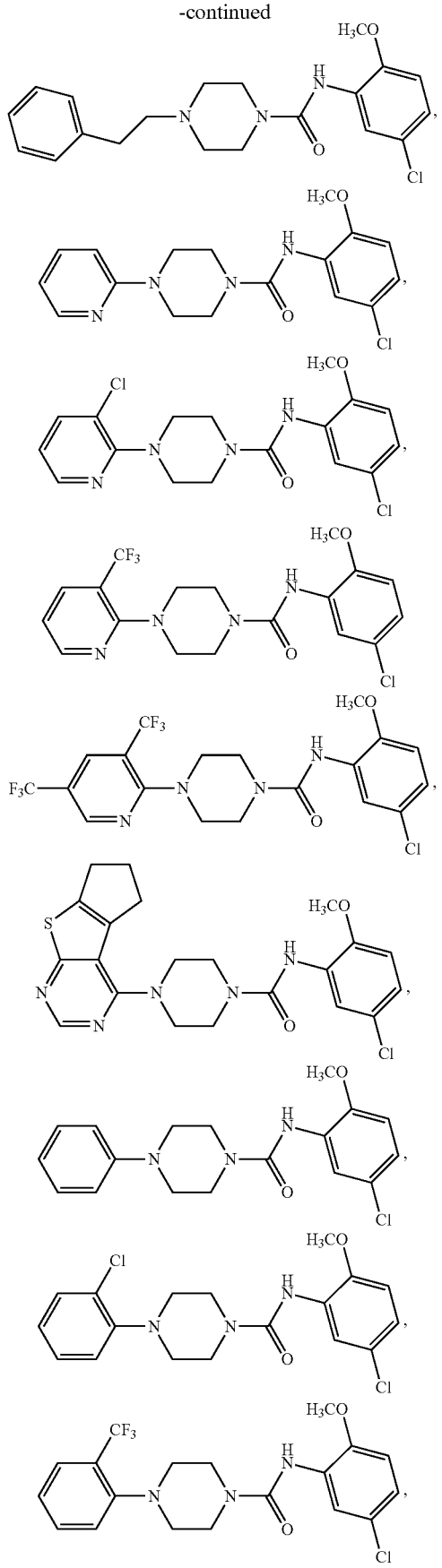
-continued
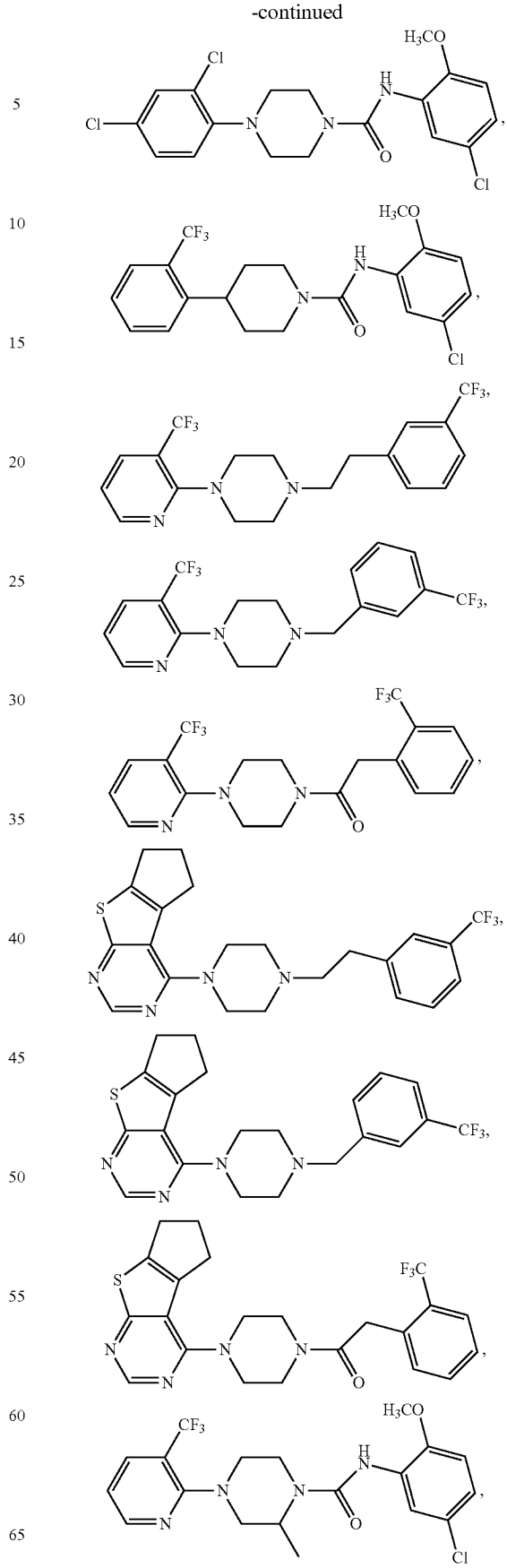

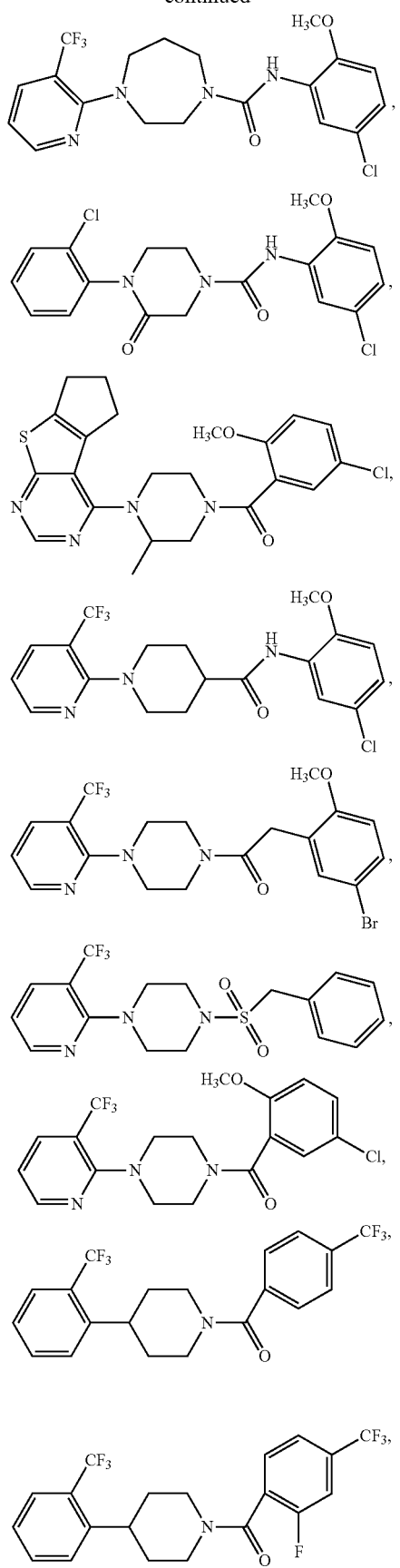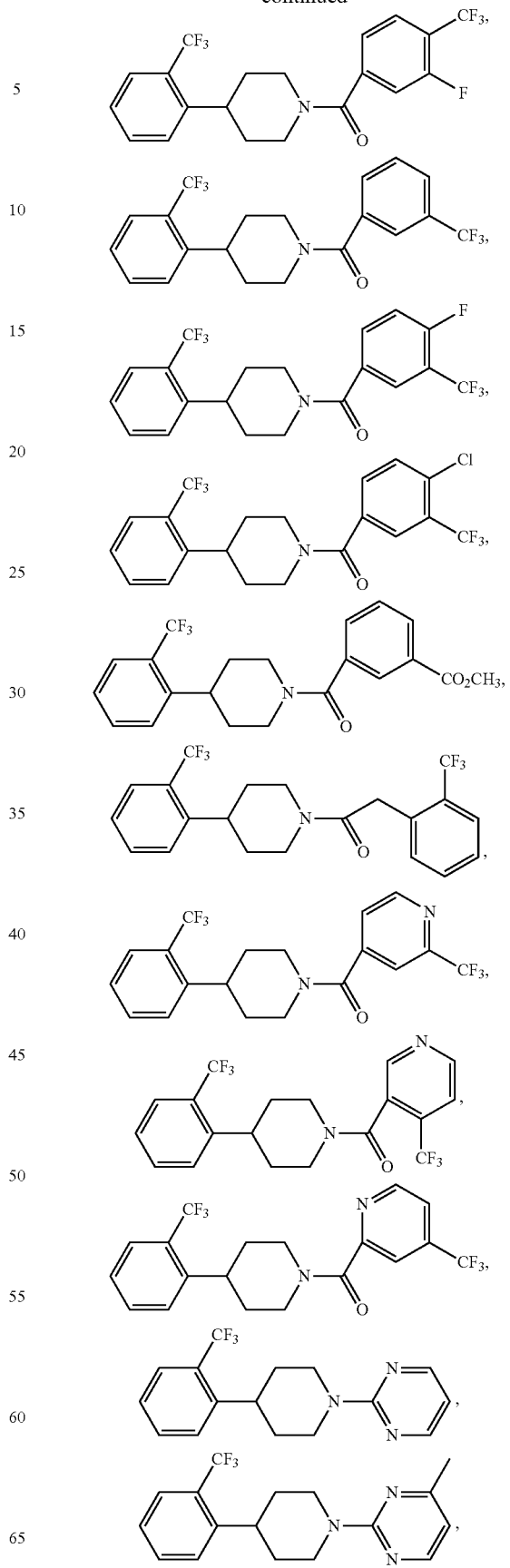

-continued
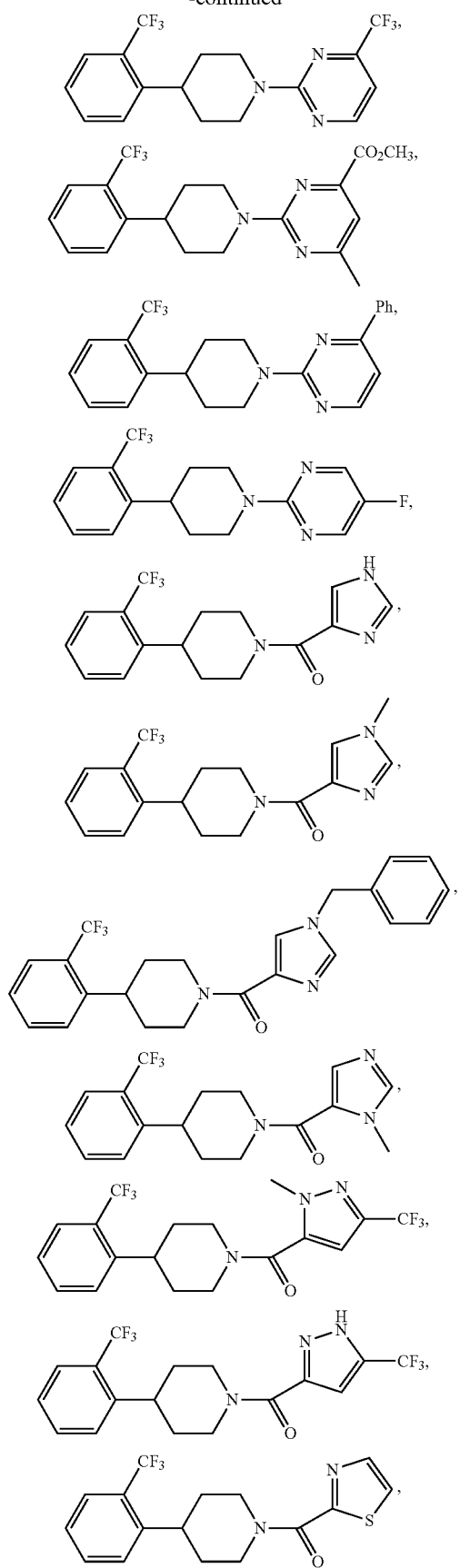
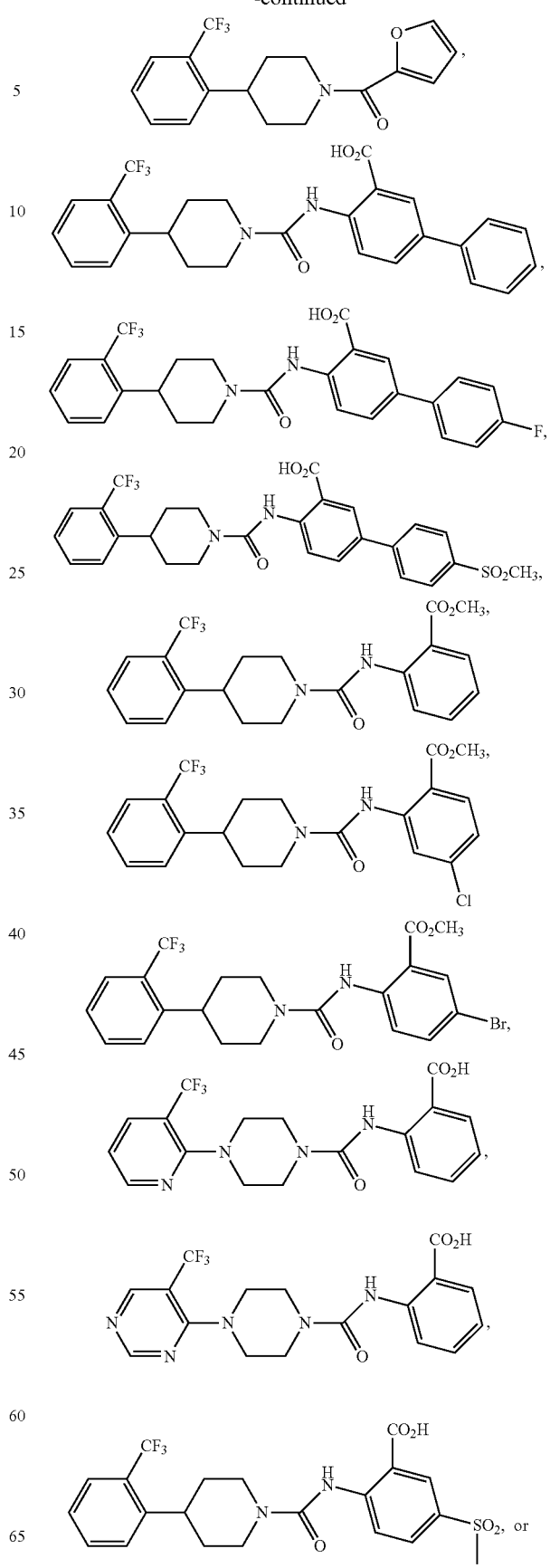

-continued

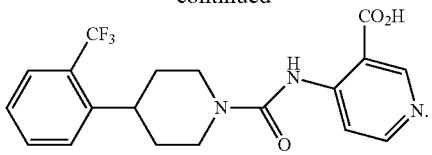

or a pharmaceutically acceptable salt thereof.

In some embodiments, the disease is further characterized by bisretinoid-mediated macular degeneration.

In some embodiments, the amount of the compound of the present method is effective to lower the serum concentration of RBP4 in the mammal.

In some embodiments, the amount of the compound of the present method is effective to lower the retinal concentration of a bisretinoid in lipofuscin in the mammal.

In some embodiments of the invention, the amount of the compound of the present method may be effective to lower the retinal concentration of a bisretinoid in lipofuscin in the mammal. In some embodiments, the bisretinoid is A2E. In some embodiments the bisretinoid is isoA2E. In some embodiments the bisretinoid is A2-DHP-PE. In some embodiments the bisretinoid is atRAL di-PE.

In some embodiments, the disease characterized by excessive lipofuscin accumulation in the retina may be Age-Related Macular Degeneration or Stargardt Disease.

In some embodiments, the disease characterized by excessive lipofuscin accumulation in the retina is Age-Related Macular Degeneration.

In some embodiments, the disease characterized by excessive lipofuscin accumulation in the retina is dry (atrophic) Age-Related Macular Degeneration.

In some embodiments, the disease characterized by excessive lipofuscin accumulation in the retina is Stargardt Disease.

In some embodiments, the disease characterized by excessive lipofuscin accumulation in the retina is Best disease.

In some embodiments, the disease characterized by excessive lipofuscin accumulation in the retina is adult vitelliform maculopathy.

In some embodiments, the disease characterized by excessive lipofuscin accumulation in the retina is Stargardt-like macular dystrophy.

In some embodiments, bisretinoid-mediated macular degeneration may be Age-Related Macular Degeneration or Stargardt Disease.

In some embodiments, the bisretinoid-mediated macular degeneration is Age-Related Macular Degeneration.

In some embodiments, the bisretinoid-mediated macular degeneration is dry (atrophic) Age-Related Macular Degeneration.

In some embodiments, the bisretinoid-mediated macular degeneration is Stargardt Disease.

In some embodiments, the bisretinoid-mediated macular degeneration is Best disease.

In some embodiments, the bisretinoid-mediated macular degeneration is adult vitelliform maculopathy.

In some embodiments, the bisretinoid-mediated macular degeneration is Stargardt-like macular dystrophy.

The bisretinoid-mediated macular degeneration may comprise the accumulation of lipofuscin deposits in the retinal pigment epithelium.

Figure 2:
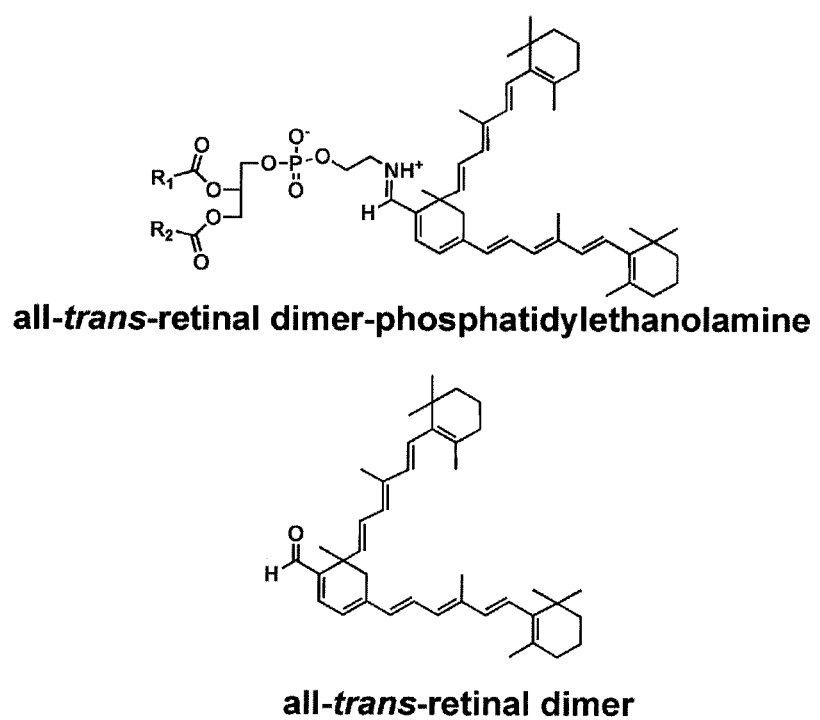
FIG. 2. Structure of bisretinoid atRAL di-PE (all-trans retinal dimer-phosphatidyl ethanolamine), a cytotoxic component of retinal lipofuscin. R1 and R2 refer to various fatty acid constituents.
Figure 3:
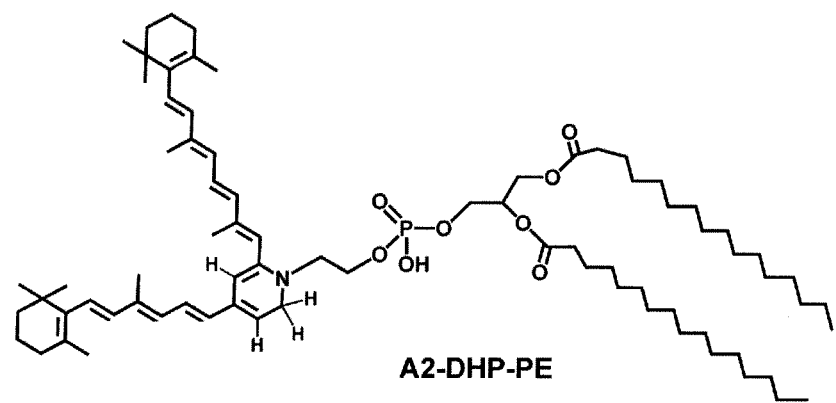
FIG. 3. Structure of bisretinoid A2-DHP-PE, a cytotoxic component of retinal lipofuscin.

As used herein, "bisretinoid lipofuscin" is lipofuscin containing a cytotoxic bisretinoid. Cytotoxic bisretinoids include but are not necessarily limited to A2E, isoA2E, atRAL di-PE, and A2-DHP-PE (FIG. 1-3).

As used herein, the description "pharmaceutically active" is used to characterize a substance, compound, or composition suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department of Health and Human Services, 30$^{th}$ edition, 2010), which are hereby incorporated by reference.

Another aspect of the invention comprises a compound used in the method of the present invention as a pharmaceutical composition.

The compounds used in the method of the present invention may may be in a salt form. As used herein, a "salt" is a salt of the instant compound which has been modified by making acid or base salts of the compounds. In the case of the use of the compounds for treatment of bisretinoid-mediated macular degeneration, the salt is pharmaceutically acceptable. Examples of pharmaceutically acceptable salts include, but are not limited to, mineral or organic acid salts of basic residues such as amines. The term "pharmaceutically acceptable salt" in this respect, refers to the relatively non-toxic, inorganic and organic base addition salts of the compounds. These salts can be prepared in situ during the final isolation and purification of the compounds, or by separately reacting purified compounds in their free acid form with a suitable organic or inorganic base, and isolating the salt thus formed.

As used herein, "treating" means slowing, stopping, or preventing the progression of a disease. An embodiment of "treating bisretinoid-mediated macular degeneration" is delaying or preventing the onset, progression, or mitigating severity of vision loss.

The compounds used in the method of the present invention may may be administered in various forms, including those detailed herein. The treatment with the compound may be a component of a combination therapy or an adjunct therapy, i.e. the mammal in need of the drug is treated or given another drug for the disease in conjunction with the compounds used in the method of the present invention. This combination therapy can be sequential therapy where the mammal is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the mammal. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of the compound and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise the compound alone, or mixtures of the compound with additional compounds used to treat lipofuscin-mediated macular degeneration. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the eye, all using dosage forms well known to those of ordinary skill in the pharmaceutical arts.

The compounds used in the method of the present invention can be administered in a mixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman at al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxy-ethylaspartamidephenol, or polyethyleneoxide-polylysine substituted with palmitoyl residues. Furthermore, The compounds used in the method of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The compounds used in the method of the present invention can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the compounds used in the method of the present invention and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the compounds used in the method of the present invention may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds used in the method of the present invention and compositions thereof of the invention can be coated onto stents for temporary or permanent implantation into the cardiovascular system of a subject.

The compounds and compositions of the present invention are useful for the prevention and treatment of lipofuscin-mediated macular degeneration.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

Each embodiment disclosed herein is contemplated as being applicable to each of the other disclosed embodiments. Thus, all combinations of the various elements described herein are within the scope of the invention.

This invention will be better understood by reference to the Examples which follow, but those skilled in the art will readily appreciate that the specific experiments detailed are only illustrative of the invention as described more fully in the claims which follow thereafter.

EXAMPLES

Example 1

Synthesis of Compound 1

The compound 2(4-(2-(trifluoromethyl)phenyl)piperidine-1-carboxamido)benzoic acid has the structure:

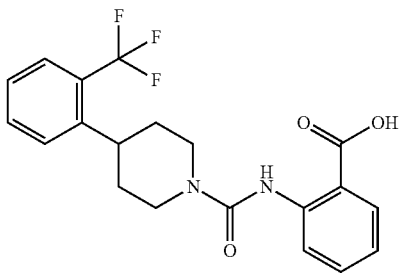 [SMILES: O=C(O)c1ccccc1NC(=O)N1CCC(c2ccccc2C(F)(F)F)CC1]

termed "Compound 1" herein, and was obtained from Sigma (Sigma-Aldrich Corp., St. Louise Mo., USA, Catalogue No. A3111). Compound 1 is described in PCT/US2011/061763, the contents of which are hereby incorporated by reference.

Compound 1, has also been called A1120 and may be made by the following techniques described in Motani et al., 2009 as follows: A solution of methyl 2-isocyanatobenzoate (10.00 g, 56.4 mmol) in tetrahydrofuran (30 ml) was slowly added to a solution of 4-(2-(trifluoromethyl)phenyl)piperidine hydrochloride (14.3 g, 53.8 mmol, Sigma) and triethylamine 99% (8.99 ml, 64.5 mmol) in tetrahydrofuran (120 ml) at 0° C. The mixture was removed from the cooling bath and stirred at room temperature for 15 min, at which time LC/MS analysis indicated that the reaction was complete. EtOH (75 ml) and aqueous LiOH (2N, 95 ml) were then added, and the solution was stirred for 6 h at room temperature. Subsequently, aqueous HCl (2N, 150 ml) was added, and the resulting mixture was extracted with EtOAc (2×600 ml). The EtOAc extract was dried over MgSO4 and concentrated to an off-white solid. Recrystallization from EtOAc yielded 14.0 g of 2-(4-(2-(trifluoromethyl)phenyl)piperidine-1-carboxamido)benzoic acid as a white solid, which was homogeneous by analytical high-performance liquid chromatography (>99%).

Example 2

TR-FRET Assay for Antagonists of Retinol-Induced RBP4-TTR Interaction

Figure 7:
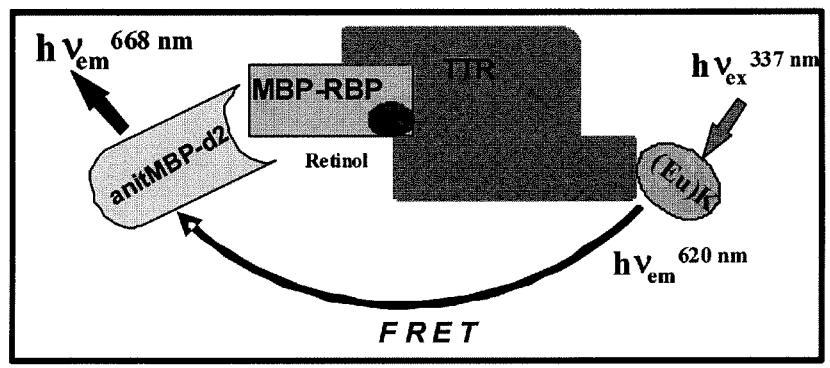
FIG. 7. Schematic depiction of the HTRF-based assay format for characterization of RBP4 antagonists disrupting retinol-induced RBP4-TTR interaction.

TR-FRET (Time-Resolved Fluorescence Resonance Energy Transfer) is an assay format that can be used in characterization of compounds affecting protein-protein interactions (31-33). The HTRF (Homogeneous Time-Resolved Fluorescence) variant of TR-FRET is the most advanced as it has improved light capturing due to the use of Eu3+ cryptates. In the presence of retinol, RBP4-TTR interaction induces FRET that can be registered as increased ratio of 668/620 fluorescence signals. Binding of a desired RBP4 antagonist displaces retinol and induces hindrance for RBP4-TTR interaction resulting in the decreased FRET signal (FIG. 7).

Figure 8:
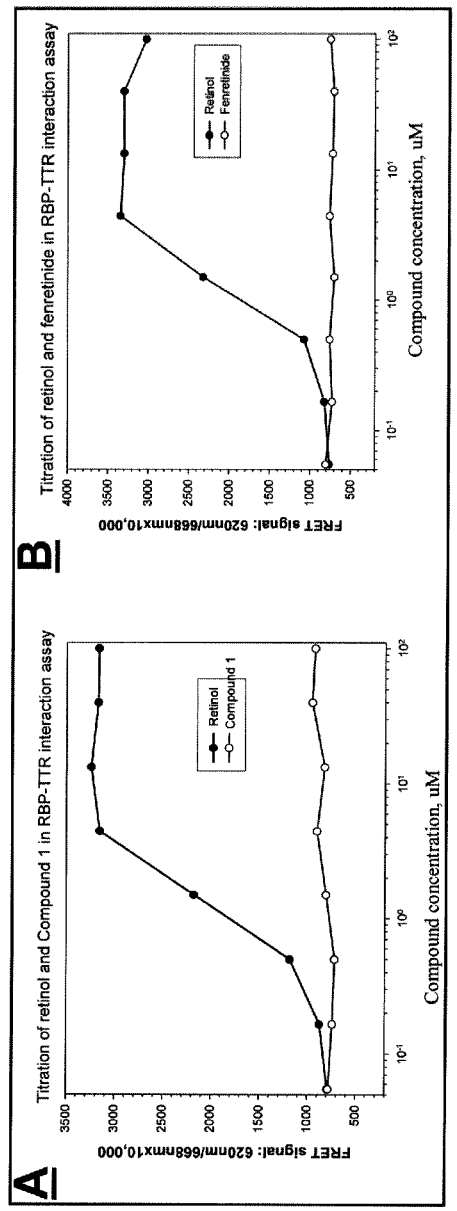
FIG. 8. Dose titrations of all-trans retinol (panels A and B, blue), Compound 1 (red, A), and fenretinide (red, B) in the HTRF-based RBP4-TTR interaction assay.

The assay was developed using *E. coli*-expressed MBP-tagged RBP4 and commercially available TTR labeled directly with Eu3+ cryptate. In addition to MBP-RBP4 and Eu3+ (K)-TTR, a detector reagent anti-MBP-d2 was present in the mix. The assay was first optimized in the agonist mode; sensitivity and dynamic range of the assay was first mode in respect to RBP4, TTR and detection reagent concentrations. In order to determine the optimum concentration of all-trans retinol stimulating the RBP4-TTR interaction eight-point titration retinol titrations were performed along with titrations of Compound 1 and fenretinide (FIG. 8). It was demonstrated that all-trans retinol stimulates RBP4-TTR interaction in a dose dependent manner (FIG. 8) with $EC_{50}$ of ~1.2 µM. As expected, RBP4 antagonists Compound 1 and fenretinide did not induce RBP4-TTR interaction (FIG. 8).

Figure 9:
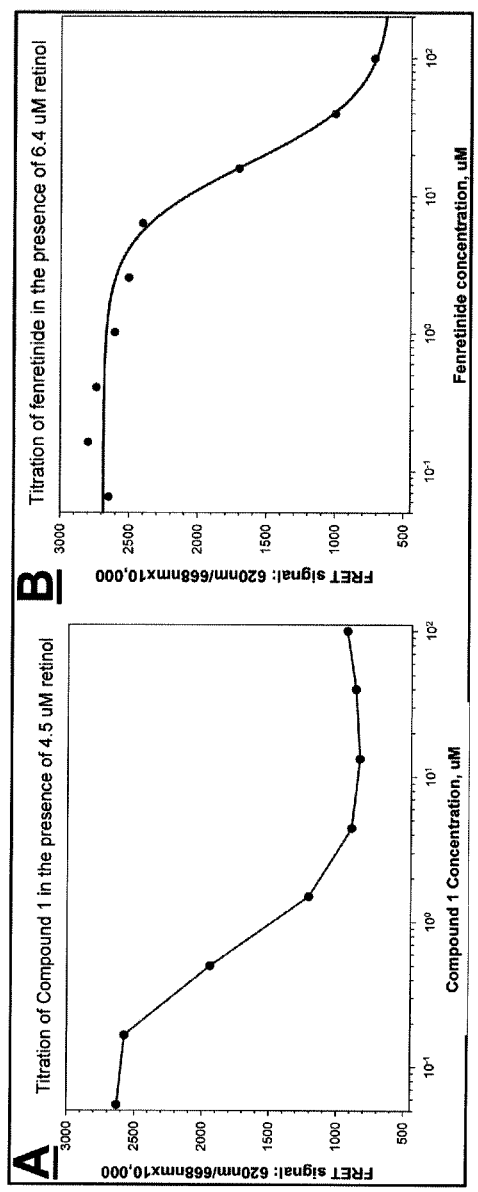
FIG. 9. Dose titrations of Compound 1 and fenretinide in the presence of all-trans retinol in the HTRF-based RBP4-TTR interaction assay.
Figure 10:
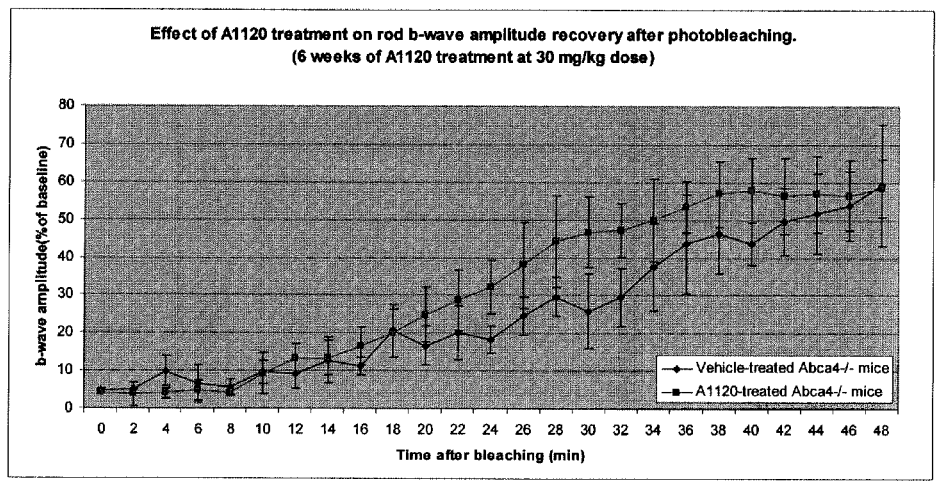
FIG. 10. Compound 1 does not reduce ERG b-wave after photobleaching.

Given that retinol is present in serum at micromolar concentrations and taking into account the results of retinol titrations, the assay was converted to the antagonist mode by testing fixed concentration of retinol within the 1-10 µM range and using the saturating 40 µM concentration of antagonists (fenretinide and Compound 1). The optimum retinol concentration in the antagonist mode in regard of assay sensitivity and dynamic range was found to be in the 4.5-6.5 µM range. Titrations of Compound 1 and fenretinide were conducted in the presence of retinol in order to characterize our starting compounds in the primary assay and prove that the assay is suitable for characterization of RBP4 antagonists (FIG. 9).

The two compounds, Compound 1 and fenretinide, antagonized the retinol-induced RBP4-TTR interaction with $EC_{50}$'s in the µM range (2.2 µM for Compound 1 and 17.3 µM for fenretinide).

Example 3

Compound 1 Efficacy in a Mammalian Model

Figure 11:
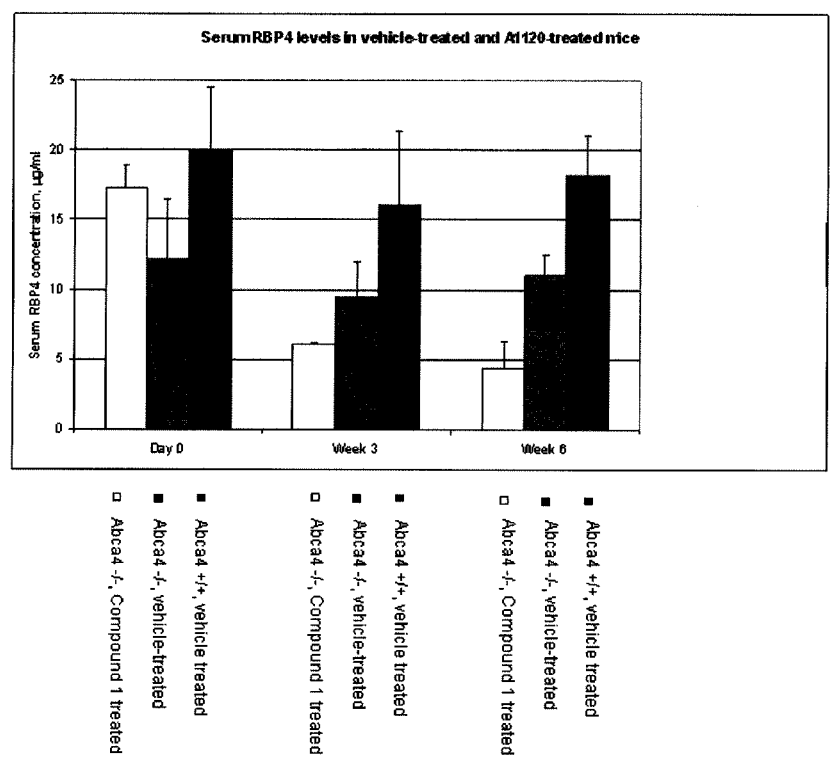
FIG. 11. Reduction in serum RBP4 in response to Compound 1 treatment. Effect of long-term oral A1120 administration on serum RBP4 in Abca4−/− mice. Serum RBP4 levels were measured with ELISA test in vehicle-treated wild-type mice (green columns), vehicle-treated Abca4−/− mice (blue columns), and A1120-treated Abca4−/− mice (red columns) at indicated timepoints. A1120 formulated in a chow was dosed at 30 mg/kg. Compared with Day 0, statistically significant 64% RBP4 reduction at Week 3 and 75% RBP4 reduction at Week 6 is seen in the A1120 treatment group ($p<0.05$). Changes in RBP4 levels at different timepoints within the vehicle-treated wild-type and vehicle-treated Abca4−/− groups were not statistically significant.
Figure 12:
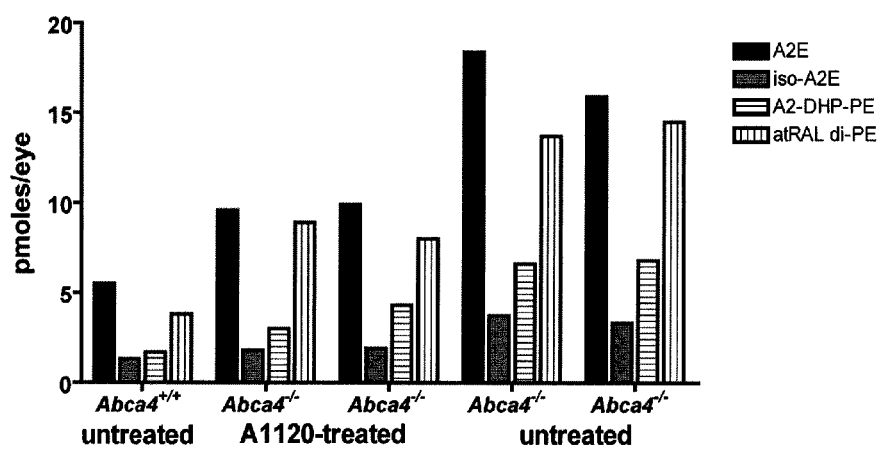
FIG. 12. Reduction of toxin bisretinoids by Compound 1.

The effectiveness of Compound 1 was tested in wild-type and Abca4−/− mice. The Abca4−/− mouse model manifests accelerated accumulation of lipofuscin in the RPE and is considered a pre-clinical efficacy model for a drug reducing lipofuscin accumulation. Compound 1 was orally dosed for 3 weeks at 30 mg/kg. There was approximately a 70% reduction in the serum RBP4 level in treated animals (FIG. 11). Additionally, it was discovered that that the levels of A2E/isoA2E and other bisretinoids were reduced by approximately 50% in treated mice (FIG. 12). The levels of A2-DHP-PE and atRAL di-PE were also reduced. These preclinical efficacy data show that Compound 1 is a potential small molecule treatment for dry AMD and Stargardt's disease.

Tissue Extraction and HPLC Analysis of Bisretinoids

Abca4/Abcr null mutant mice (albino) homozygous for Rpe65-Leu450 are bred genotyped and housed. Posterior eyecups of mice and RPE/choroids harvested from human donor eyes (National Disease Research Interchange, Philadelphia Pa.) are homogenized in phosphate buffered saline (PBS) using a glass tissue grinder and extracted in chloroform/methanol (2:1). Extracts are subsequently filtered through cotton and passed through a reverse phase cartridge (C8 Sep-Pak, Millipore) with 0.1% TFA (Aldrich Chemical Company, Milwaukee, Wis.) in methanol. After evaporation of solvent under argon gas, the extract is dissolved in 50% methanolic chloroform containing 0.1% TFA. An Alliance system (Waters, Corp, Milford, Mass.) equipped with 2695 Separation Module, 2996 Photodiode Array Detector, a 2475 Multi λ Fluorescence Detector and operating with Empower® software is used for HPLC analysis. An Atlantis® dC18 column (3 µm, 4.6×150 mm, Waters, USA) and a Delta Pak® C4 column (5 µm, 3.9×150 mm, Waters, USA) are employed. Gradients of water and acetonitrile (Fisher, Fair Lawn, N.J.) with 0.1% of TFA are used for mobile phase; details are provided in figure legends. HPLC quantification is carried out using the Empower® software to determine peak areas. Detection by photodiode array is set at 430 and 490 nm. Molar quantity per murine eye is determined using calibration curves constructed from known concentrations of purified external standards and by normalizing to the ratio of the HPLC injection volume (10 µL) versus total extract volume.

Example 4

TR-FRIT Assay for Retinol-Induced RBP4-TTR Interaction

Bacterially expressed MBP-RBP4 and untagged TTR were used in this assay. For the use in the TR-FRET assay the maltose binding protein (MBP)-tagged human RBP4 fragment (amino acids 19-201) was expressed in the Gold(DE3) pLysS *E. coli* strain (Stratagene) using the µMAL-c4x vector. Following cell lysis, recombinant RBP4 was purified from the soluble fraction using the ACTA FPLC system (GE Healthcare) equipped with the 5-ml the MBP Trap HP column. Human untagged TTR was purchased from Calbiochem. Untagged TTR was labeled directly with $Eu^{3+}$ Cryptate-NHS using the HTRF Cryptate Labeling kit from CisBio following the manufacturer's recommendations. HTRF assay was performed in white low volume 384 well plates (Greiner-Bio) in a final assay volume of 16 µl per well. The reaction buffer contained 10 mM Tris-HCl pH 7.5, 1 mM DTT, 0.05% NP-40, 0.05% Prionex, 6% glycerol, and 400 mM KF. Each reaction contained 60 nM MBP-RBP4 and 2 nM TTR-Eu along with 26.7 nM of anti-MBP antibody conjugated with d2 (Cisbio). Titration of test compounds in this assay was conducted in the presence of 1 µM retinol. All reactions were assembled in the dark under dim red light and incubated overnight at +4° C. wrapped in aluminum foil. TR-FRET signal was measured in the SpectraMax M5e Multimode Plate Reader (Molecular Device). Fluorescence was excited at 337 nm and two readings per well were taken: Reading 1 for time-gated energy transfer from Eu(K) to d2 (337 nm excitation, 668 nm emission, counting delay 75 microseconds, counting window 100 microseconds) and Reading 2 for Eu(K) time-gated fluorescence (337 nm excitation, 620 nm emission, counting delay 400 microseconds, counting window 400 microseconds). The TR-FRET signal was expressed as the ratio of fluorescence intensity: $Flu_{665}/Flu_{620} \times 10,000$.

Example 5

Scintillation Proximity RBP4 Binding Assay

Untagged human RBP4 purified from urine of tubular proteinuria patients was purchased from Fitzgerald Industries International. It was biotinylated using the EZ-Link Sulfo-NHS-LC-Biotinylation kit from Pierce following the manufacturer's recommendations. Binding experiments were performed in 96-well plates (OptiPlate, PerkinElmer) in a final assay volume of 100 µl per well in SPA buffer (1×PBS, pH 7.4, 1 mM EDTA, 0.1% BSA, 0.5% CHAPS). The reaction mix contained 10 nM $^3$H-Retinol (48.7 Ci/mmol; PerkinElmer), 0.3 mg/well Streptavidin-PVT beads, 50 nM biotinylated RBP4 and a test compound. Nonspecific binding was determined in the presence of 20 µM of unlabeled retinol. The reaction mix was assembled in the dark under dim red light. The plates were sealed with clear tape (TopSeal-A: 96-well microplate, PerkinElmer), wrapped in the aluminum foil, and allowed to equilibrate 6 hours at room temperature followed by overnight incubation at +4° C. Radiocounts were measured using a TopCount NXT counter (Packard Instrument Company).

Example 6

Animal Studies

Ten week-old Abca4 null mutant mice (129/SV×C57BL/6J) bred as previously described were used in the study. Abca4−/− (knockout) and Abca4+/+(wild-type) mice were raised under 12 h on-off cyclic lighting with an in-cage illuminance of 30-50 lux. For long-term oral dosing A1120 was formulated into Purina 5035 rodent chow at Research Diets, Inc. (New Brunswick, N.J.) to ensure consistent 30 mg/kg daily oral dosing. Animals were administered the A1120-containing chow for 6 weeks.

Example 7

Serum RBP4 Measurements

Blood samples were collected from a tail vein at days 0, 21 and 42 of the A1120 dosing. Whole blood was drawn into a centrifuge tube and was let clot at room temperature for 30 min followed by centrifugation at 2,000×g for 15 minutes at +4° C. to collect serum. Serum RBP4 was measured using the RBP4 (mouse/rat) dual ELISA kit (Enzo Life Sciences) following the manufacturer's instructions.

Example 8

Biretinoid Extraction and Analysis

Following euthanasia, posterior eye cups were pooled and homogenized in PBS using a tissue grinder. An equal volume of a mixture of chloroform and methanol (2:1) was added, and the sample was extracted three times. To remove insoluble material, extracts were filtered through cotton and passed through a reverse phase (C18 Sep-Pak, Millipore) cartridge with 0.1% TFA in methanol. After the solvent had been removed by evaporation under argon gas, the extract was dissolved in methanol containing 0.1% TFA, for HPLC analysis. For quantification of bisretinoids of RPE lipofuscin, a Waters Alliance 2695 HPLC system was employed with an Atlantis dC18 column (Waters, 4.6 mm×150 mm, 3 µm) and the following gradient of acetonitrile in water (containing 0.1% trifluoroacetic acid): 90 to 100% from 0 to 10 min and 100% acetonitrile from 10 to 20 min, with a flow rate of 0.8 mL/min with monitoring at 430 nm. The injection volume was 10 µL. Extraction and injection for HPLC were performed under dim red light. Levels of bisretinoid were determined by reference to external standards of HPLC-purified compound.

Example 9

Small Molecule Derivatives of Compound 1

An additional aspect of the invention provides compounds (Table 1) used in the method of the present invention that are expected to function analogously to Compound 1 and which are synthesized by a similar synthetic route. Further, those having ordinary skill in the art of organic synthesis will appreciate that modifications to general procedures described herein and synthetic routes contained in this application can be used to synthesize compounds used in the method of the present invention. Suitable organic transformations are described in March's Advanced Organic Chemistry: Reactions, Mechanisms, and Structure (Wiley-Interscience; 6$^{th}$ edition, 2007), the content of which is hereby incorporated by reference.

TABLE 1

| Compound # | Structure |
| --- | --- |
| 1A | (structure shown) |

TABLE 1-continued

| Compound # | Structure |
|---|---|
| 2 | (4-methylpiperazine-1-carboxylic acid (5-chloro-2-methoxyphenyl)amide) |
| 3 | (4-(pyrimidin-2-yl)piperazine-1-carboxylic acid (5-chloro-2-methoxyphenyl)amide) |
| 4 | (4-(furan-2-carbonyl)piperazine-1-carboxylic acid (5-chloro-2-methoxyphenyl)amide) |
| 5 | (4-(2,6-dichlorobenzyl)piperazine-1-carboxylic acid (5-chloro-2-methoxyphenyl)amide) |
| 6 | (4-phenethylpiperazine-1-carboxylic acid (5-chloro-2-methoxyphenyl)amide) |
| 7 | (4-(pyridin-2-yl)piperazine-1-carboxylic acid (5-chloro-2-methoxyphenyl)amide) |
| 8 | (4-(3-chloropyridin-2-yl)piperazine-1-carboxylic acid (5-chloro-2-methoxyphenyl)amide) |
| 9 | (4-(3-(trifluoromethyl)pyridin-2-yl)piperazine-1-carboxylic acid (5-chloro-2-methoxyphenyl)amide) |
| 10 | (4-(3,5-bis(trifluoromethyl)pyridin-2-yl)piperazine-1-carboxylic acid (5-chloro-2-methoxyphenyl)amide) |
| 11 | (4-(6,7-dihydro-5H-cyclopenta[4,5]thieno[2,3-d]pyrimidin-4-yl)piperazine-1-carboxylic acid (5-chloro-2-methoxyphenyl)amide) |
| 12 | (4-phenylpiperazine-1-carboxylic acid (5-chloro-2-methoxyphenyl)amide) |
| 13 | (4-(2-chlorophenyl)piperazine-1-carboxylic acid (5-chloro-2-methoxyphenyl)amide) |
| 14 | (4-(2-(trifluoromethyl)phenyl)piperazine-1-carboxylic acid (5-chloro-2-methoxyphenyl)amide) |
| 15 | (4-(2,4-dichlorophenyl)piperazine-1-carboxylic acid (5-chloro-2-methoxyphenyl)amide) |

TABLE 1-continued
| Compound # | Structure |
|---|---|
| 16 | 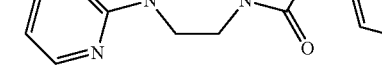 |
| 17 | 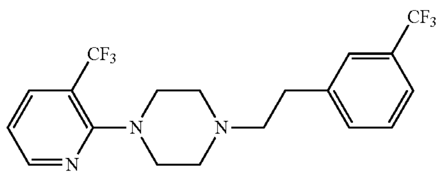 [SMILES: FC(F)(F)c1cccc(CCN2CCN(c3ncccc3C(F)(F)F)CC2)c1] |
| 18 | 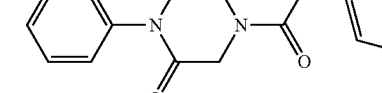 |
| 19 | 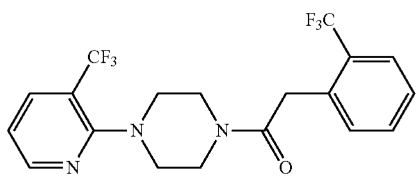 [SMILES: O=C(Cc1ccccc1C(F)(F)F)N1CCN(c2ncccc2C(F)(F)F)CC1] |
| 20 | 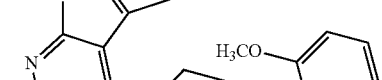 |
| 21 | 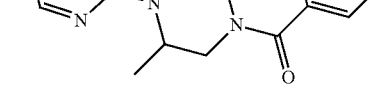 |
| 22 | 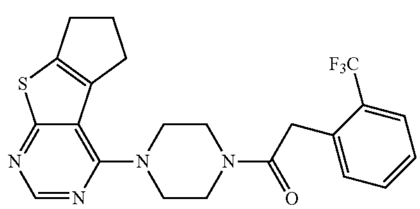 [SMILES: O=C(Cc1ccccc1C(F)(F)F)N1CCN(c2ncnc3sc4c(c23)CCC4)CC1] |
| 23 | 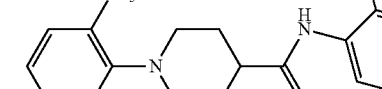 |
| 24 | |
| 25 | |
| 26 | |
| 27 | |
| 28 | |
| 29 | |
| 30 | |
| 31 | |

TABLE 1-continued

| Compound # | Structure |
|---|---|
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |
| 49 | (structure) |

TABLE 1-continued

| Compound # | Structure |
|---|---|
| 50 | (structure) |
| 51 | (structure) |
| 52 | (structure) |
| 53 | (structure) |
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |
| 64 | (structure) |
| 65 | (structure) |

Example 10

Correlation Between A1120-Induced Serum RBP4 Reduction and Inhibition of Bisretinoid Accumulation in the Retina To determine whether A1120 has an effect on retinal production of lipofuscin fluorophores we administered the compound at the daily 30 mg/kg dose to Abca4−/− mice for a period of 6 weeks. Blood samples collected from the treatment and control groups at baseline, Day 21 and Day 42 were used to measure serum RBP4 in order to correlate RBP4 levels with reduction in formation of lipofuscin bisretinoids.

Figure 13:
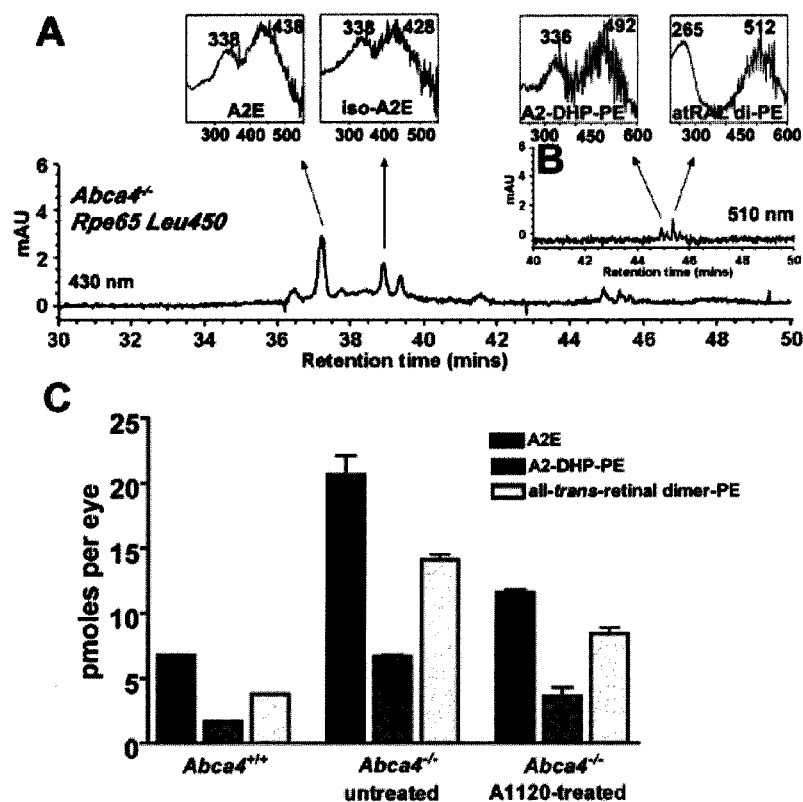
FIG. 13. Effect of A1120 treatment on the levels of lipofuscin fluorophores in eyes of the Abca4−/− mice. Bisretinoids were extracted from the eyecups of vehicle-treated wild-type mice, vehicle-treated Abca4−/− mice, and A1120-treated Abca4−/− mice after 6 weeks of dosing and analyzed by HPLC. 13A: The representative reverse phase HPLC chromatogram (monitoring at 430 nm) of an extract from eyecups of A1120-treated Abca4−/− mice. Insets on the top show UV-visible absorbance spectra of A2E and iso-A2E. 13B: Chromatographic monitoring at 510 nm, retention time 40-50 minutes, for A2-DHP-PE (A2-dihydropyridine-phosphatidylethanolamine) and atRALdi-PE (all-transretinal dimmer-phosphatidylethanolamine) detection with insets on the top showing absorbance UV-visible spectra of A2-DHP-PE and atRALdi-PE. 13C: Levels of A2E, A2-DHP-PE and atRALdi-PE in vehicle-treated wild-type mice, vehicle-treated Abca4−/− mice, and A1120-treated Abca4−/− mice after 6 weeks of dosing showing 45-50% reduction in bisretinoid levels in response to A1120 treatment.
Figure 14A:
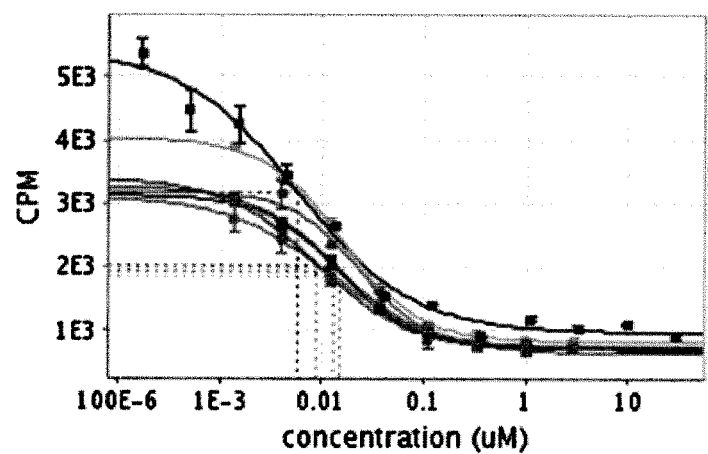
FIG. 14A: Analysis of Compound 1 in SPA-based RBP4 binding assay. Titration was conducted 7 times. $IC_{50}$ values calculated in seven experiments were 0.00579, 0.0229, 0.0148, 0.0138, 0.0126, 0.0156 and 0.00901 (in μM).
Figure 14B:
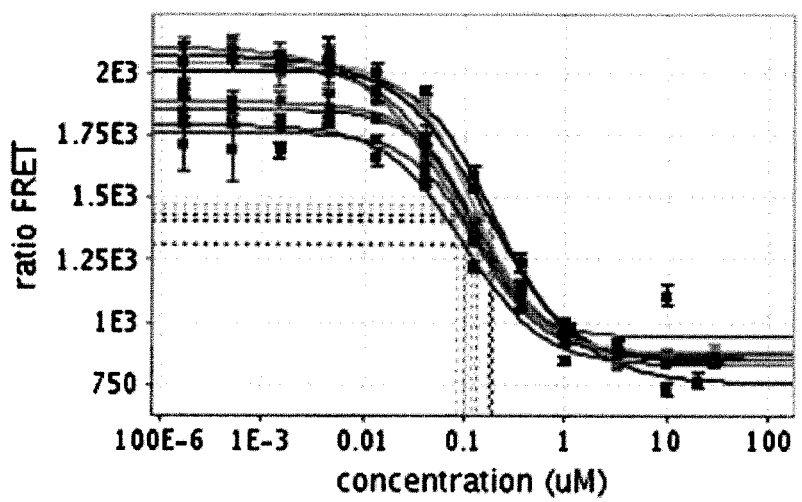
FIG. 14B: Analysis of Compound 1 in HTRF-based retinol-dependent RBP4-TTR interaction assay. Titration was conducted 9 times. $IC_{50}$ values calculated in nine experiments were 0.182, 0.119, 0.195, 0.139, 0.101, 0.109, 0.0848, 0.126 and 0.134 (in μM).
Figure 14C:
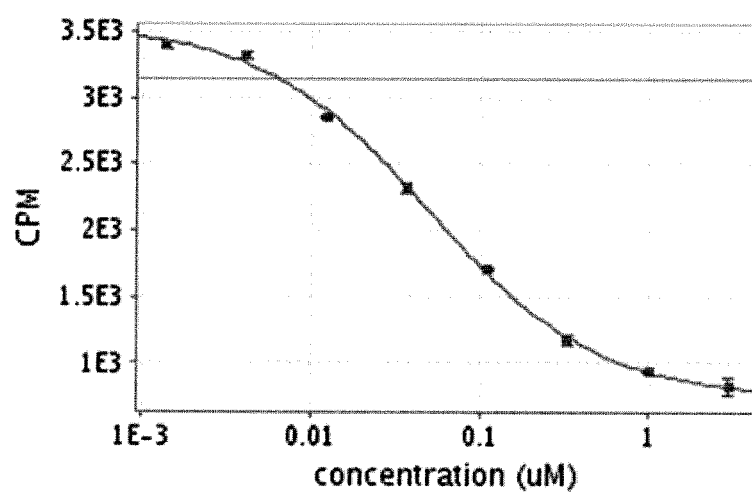
FIG. 14C: Analysis of Compound 64 in SPA-based RBP4 binding assay. $IC_{50}$ value calculated in this experiment was 0.0498 μM.
Figure 14D:
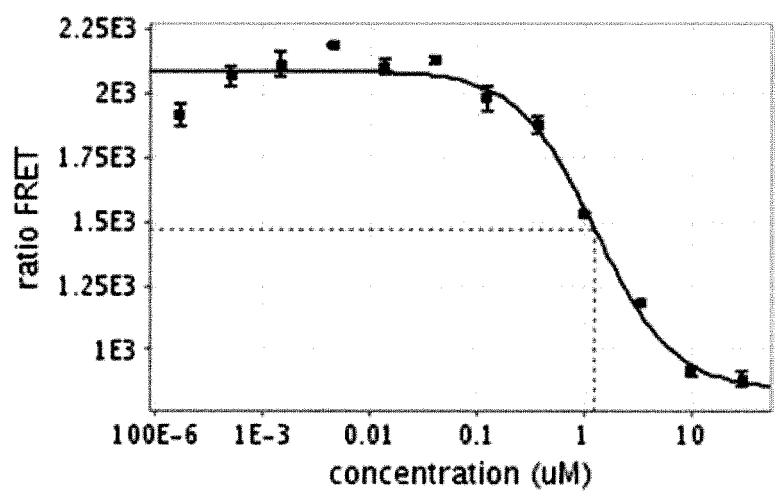
FIG. 14D: Analysis of Compound 64 in HTRF-based retinol-dependent RBP4-TTR interaction assay. $IC_{50}$ value calculated in this experiment was 1.27 μM.
Figure 14E:
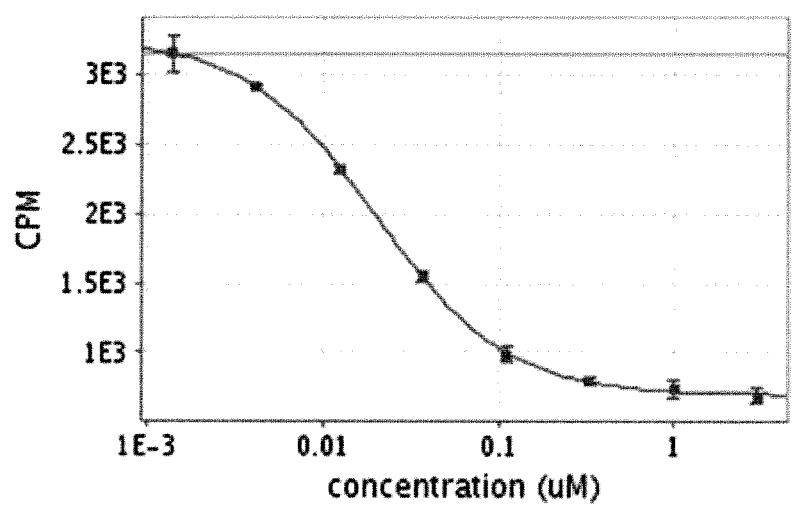
FIG. 14E: Analysis of Compound 65 in SPA-based RBP4 binding assay. $IC_{50}$ value calculated in this experiment was 0.0199 μM.
Figure 14F:
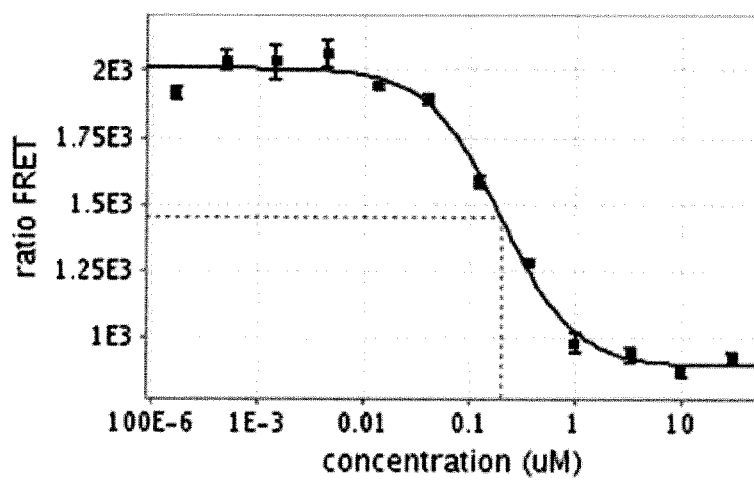
FIG. 14F: Analysis of Compound 65 in HTRF-based retinol-dependent RBP4-TTR interaction assay. $IC_{50}$ value calculated in this experiment was 0.199 μM.
Figure 14G:
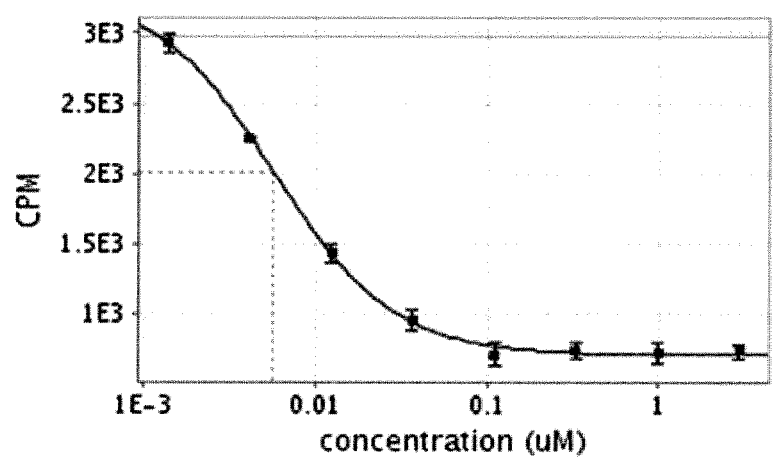
FIG. 14G. Analysis of Compound 48 in SPA-based RBP4 binding assay. $IC_{50}$ value calculated in this experiment was 0.00568 μM.
Figure 14H:
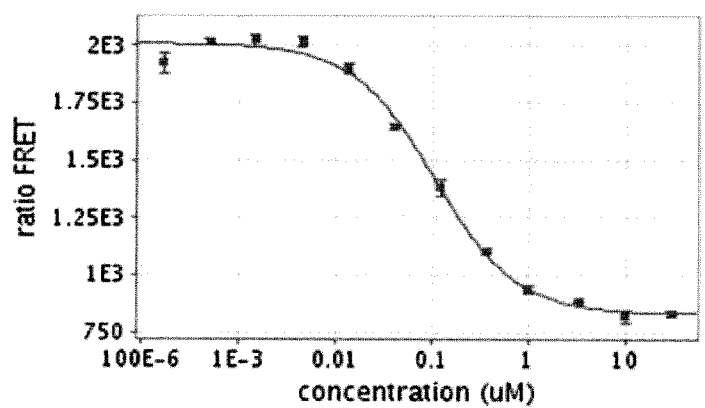
FIG. 14H: Analysis of Compound 48 in HTRF-based retinol-dependent RBP4-TTR interaction assay. $IC_{50}$ value calculated in this experiment was 0.106 μM.

As shown in FIG. 13, chronic oral administration of A1120 at 30 mg/kg to Abca4−/− mice induced a 64% decrease in serum RBP4 level at Day 21 and a 75% decrease at Day 42. Levels of lipofuscin fluorophores (A2E, A2-DHP-PE and all-trans-retinal dimer-PE) were determined at the end of the 42-day treatment period using quantitative HPLC.

Representative chromatogram of lipofuscin fluorophores from eyecups of vehicle-treated Abca4−/− mice along with absorbance spectra for the indicated peaks is shown in FIGS. 14, A and B. As shown in FIG. 14, C the levels of bisretinoid accumulation were 3-4 times higher in the vehicle-treated Abca4−/− mice than in wild-type controls. Administration of A1120 reduces the production of A2E, A2-DHP-PE, and atRAL di-PE in A1120-treated Abca4−/− mice in comparison to the vehicle-treated Abca4−/− animals by approximately 50%. This result clearly demonstrated that A1120 can inhibit in vivo accumulation of toxic lipofuscin bisretinoids in the animal model of enhanced lipofuscinogenesis. We did not note any obvious signs of compound toxicity such as weight loss or reduction in food consumption during the 6 week-long chronic A1120 dosing.

Example 11

RPB4 Binding of Derivatives of Compound 1

Compounds 1, 64, 65 and 48 were studied in two in vitro assays, RBP4 binding (SPA) and retinol-dependent RBP4-TTR interaction (HTRF) (FIG. 15). The compounds bind to RBP4 and antagonize retinol-dependent RBP4-TTR interaction implying that compounds may reduce the level of serum RBP4 and retinol.

DISCUSSION

Age-related macular degeneration (AND) is the leading cause of blindness in developed countries. Its prevalence is higher than that of Alzheimer's disease. There is no treatment for the most common dry form of AND. Dry AND is triggered by abnormalities in the retinal pigment epithelium (RPE) that lies beneath the photoreceptor cells and provides critical metabolic support to these light-sensing cells. RPE dysfunction induces secondary degeneration of photoreceptors in the central part of the retina called the macula. Experimental data indicate that high levels of lipofuscin induce degeneration of RPE and the adjacent photoreceptors in atrophic AND retinas. In addition to AND, dramatic accumulation of lipofuscin is the hallmark of Stargardt's disease (STGD), an inherited form of juvenile onset macular degeneration. The major cytotoxic component of RPE lipofuscin is a pyridinium bisretinoid A2E. A2E formation occurs in the retina in a non-enzymatic manner and can be considered a by-product of a properly functioning visual cycle. Given the established cytotoxic affects of A2E on RPE and photoreceptors, inhibition of A2E formation could lead to delay in visual loss in patients with dry AND and STGD. It was suggested that small molecule visual cycle inhibitors may reduce the formation of A2E in the retina and prolong RPE and photoreceptor survival in patients with dry AND and STGD. Rates of the visual cycle and A2E production in the retina depend on the influx of all-trans retinol from serum to the RPE. RPE retinol uptake depends on serum retinol concentrations. Pharmacological downregulation of serum retinol is a valid treatment strategy for dry AMD and STGD. Serum retinol is maintained in circulation as a tertiary complex with retinol-binding protein (RBP4) and transthyretin (TTR). Without interacting with TTR, the RBP4-retinol complex is rapidly cleared due to glomerular filtration. Retinol binding to RBP4 is required for formation of the RBP4-TTR complex; apo-RBP4 does not interact with TTR. Importantly, the retinol-binding site on RBP4 is sterically proximal to the interface mediating the RBP4-TTR interaction. Without wishing to be bound by any scientific theory, the data herein show that small molecule RBP4 antagonists displacing retinol from RBP4 and disrupting the RBP4-TTR interaction will reduce serum retinol concentration, inhibit retinol uptake into the retina and act as indirect visual cycle inhibitors reducing formation of cytotoxic A2E.

Serum RBP4 as a Drug Target for Pharmacological Inhibition of the Visual Cycle

Figure 4:
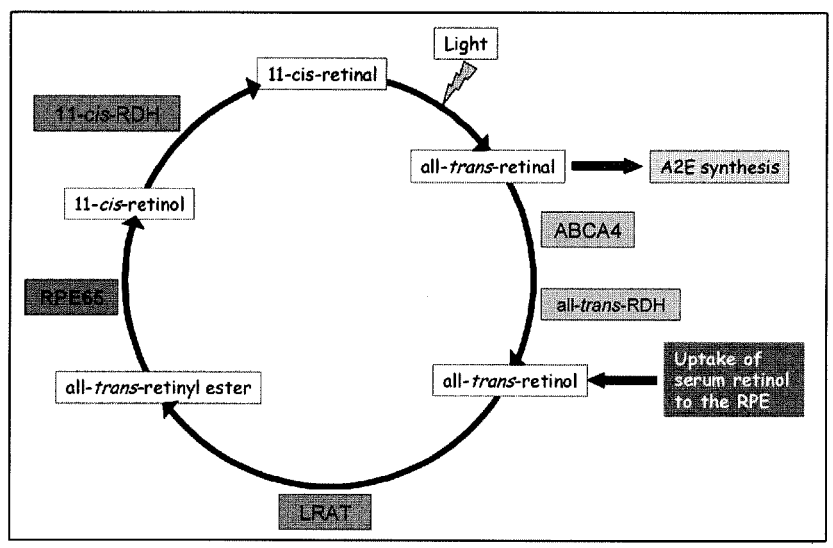
FIG. 4. Visual cycle and biosynthesis of A2E. A2E biosynthesis begins when a portion of all-trans-retinal escapes the visual cycle (yellow box) and non-enzymatically reacts with phosphatidyl-ethanolamine forming the A2E precursor, A2-PE. Uptake of serum retinol to the RPE (gray box) fuels the cycle.
Figure 5:
FIG. 5. Three-dimensional structure of the RBP4-TTR-retinol complex. Tetrameic TTR is shown in blue, light blue, green and yellow. RBP is shown in red and retinol is shown in gray (28).
Figure 6:
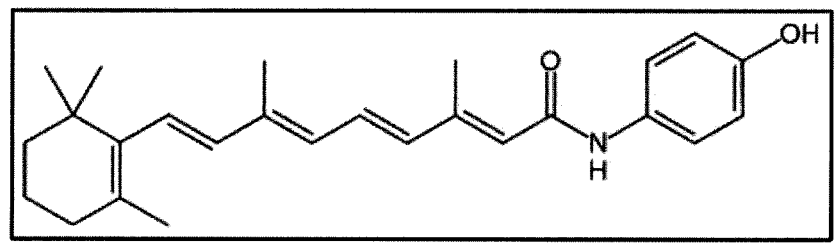
FIG. 6. Structure of fenretinide, [N-(4-hydroxy-phenyl) retinamide, 4HRP], a retinoid RBP4 antagonist.

As rates of the visual cycle and A2E production in the retina depend on the influx of all-trans retinol from serum to the RPE (FIG. 4), it has been suggested that partial pharmacological down-regulation of serum retinol may represent a target area in dry AMD treatment (11). Serum retinol is bound to retinol-binding protein (RBP4) and maintained in circulation as a tertiary complex with RBP4 and transthyretin (TTR) (FIG. 5). Without interacting with TTR, the RBP4-retinol complex is rapidly cleared from circulation due to glomerular filtration. Additionally, formation of the RBP4-TTR-retinol complex is required for receptor-mediated all-trans retinol uptake from serum to the retina.

Without wishing to be bound by any scientific theory, visual cycle inhibitors may reduce the formation of toxic bisretinoids and prolong RPE and photoreceptor survival in dry AMD. Rates of the visual cycle and A2E production depend on the influx of all-trans retinol from serum to the RPE.

Formation of the tertiary retinol-binding protein 4 (RBP4)-transthyretin (TTR)-retinol complex in serum is required for retinol uptake from circulation to the RPE. Retinol-binding site on RBP4 is sterically proximal to the interface mediating the RBP4-TTR interaction. RBP4 antagonists that compete with serum retinol for binding to RBP4 while blocking the RBP4-TTR interaction would reduce serum retinol, slow down the visual cycle, and inhibit formation of cytotoxic bisretinoids.

RBP4 represents an attractive drug target for indirect pharmacological inhibition of the visual cycle and A2E formation. The retinol-binding site on RBP4 is sterically proximal to the interface mediating the RBP4-TTR interaction. Retinol antagonists competing with serum retinol for binding to RBP4 while blocking the RBP4-TTR interaction would reduce serum RBP4 and retinol levels which would lead to reduced uptake of retinol to the retina. The outcome would be visual cycle inhibition with subsequent reduction in the A2E synthesis.

A synthetic retinoid called fenretinide [N-(4-hydroxy-phenyl)retinamide, 4HRP] previously considered as a cancer treatment (29) was found to bind to RBP4, displace all-trans retinol from RBP4 (13), and disrupt the RBP4-TTR interaction (13,14).

Fenretinide was shown to reduce serum RBP4 and retinol (15), inhibit ocular all-trans retinol uptake and slow down the visual cycle (11). Importantly, fenretinide administration reduced A2E production in an animal model of excessive bisretinoid accumulation, Abca4−/− mice (11). Pre-clinical experiments with fenretinide validated RBP4 as a drug target for dry AND. However, fenretinide is non-selective and toxic.

Independent of its activity as an antagonist of retinol binding to RBP4, fenretinide is an extremely active inducer of apoptosis in many cell types (16-19), including the retinal pigment epithelium cells (20). It has been suggested that fenretinide's adverse effects are mediated by its action as a ligand of a nuclear receptor RAR (21-24). Additionally, similar to other retinoids, fenretinide is reported to stimulate formation of hemangiosarcomas in mice. Moreover, fenretinide is teratogenic, which makes its use problematic in Stargardt disease patients of childbearing age.

As fenretinide's safety profile may be incompatible with long-term dosing in individuals with blinding but non-life threatening conditions, identification of new classes of RBP4 antagonists is of significant importance. Compound 1, a non-retinoid RBP4 ligand, was originally identified in a screen for compounds that may improve insulin sensitivity. It was confirmed that Compound 1 displaces retinol from RBP4, disrupt retinol-induced RBP4-TTR interaction, and reduce serum REBP4 levels. In addition, it was established that Compound 1 inhibits bisretinoid accumulation in the Abca4−/− mouse model of excessive lipofuscinogenesis which justifies additional evaluation of Compound 1 and its analogues as a treatment for dry AMD and Stargardt disease.

The present invention relates to small molecule derivatives of Compound 1 for treatment of macular degeneration and Stargardt Disease. Disclosed herein is the ophthalmic use of small molecule derivatives of Compound 1, 2(4-(2-(trifluoromethyl)phenyl)piperidine-1-carboxamido)benzoic acid, which is a non-retinoid RBP4 antagonist. Compound 1 was originally developed as an anti-diabetic agent (12). However, its administration did not improve insulin sensitivity in mouse diabetes models.

The small molecule derivatives disclosed herein are expected to behave analogously to Compound 1. The small molecule derivatives disclosed herein are expected to behave analogously to Compounds 64, 65 and 48. The small molecule derivatives disclosed herein have all been found to bind RBP4 in vitro. Compound 1 as well as compounds 17, 20, 21, 22, 32, 33, 34, 35, 36, 37, 38, 39, 40, 41, 42, 43, 44, 45, 46, 47, 49, 50, 51, 525, 53, 54, 55, 56, 57, 58, 59, 60, 61, 63, 64 and 65 have been shown to antagonize RBP4-TTR interaction in vitro at biologically significant concentrations.

Currently, there is no FDA-approved treatment for dry AMD or Stargardt disease, which affects millions of patients. An over the counter, non FDA-approved cocktail of antioxidant vitamins and zinc (AREDS formula) is claimed to be beneficial in a subset of dry AMD patients. There are no treatments for Stargardt disease. The present invention identified non-retinoid RBP4 antagonists that are useful for the treatment of dry AND and other conditions characterized by excessive accumulation of lipofuscin. Without wishing to be bound by any scientific theory, as accumulation of lipofuscin seems to be a direct cause of RPE and photoreceptor demise in AMD and STGD retina, the compounds described herein are disease-modifying agents since they directly address the root cause of these diseases. The present invention provides novel methods of treatment that will preserve vision in AMD and Stargardt disease patients, and patients' suffering from conditions characterized by excessive accumulation of lipofuscin.

REFERENCES

1. Petrukhin K. New therapeutic targets in atrophic age-related macular degeneration. Expert Opin. Ther. Targets. 2007, 11(5): 625-639
2. C. Delori, D. G. Goger and C. K. Dorey, Age-related accumulation and spatial distribution of lipofuscin in RPE of normal subjects. Investigative Ophthalmology and Visual Science 42 (2001), pp. 1855-1866
3. F. C. Delori, RPE lipofuscin in ageing and age-related macular degeneration. In: G. Coscas and F. C. Piccolino, Editors, Retinal Pigment Epithelium and Macular Disease (Documenta Ophthalmologica) vol. 62, Kluwer Academic Publishers, Dordrecht, The Netherlands (1995), pp. 37-45.
4. C. K. Dorey, G. Wu, D. Ebenstein, A. Garsd and J. J. Weiter, Cell loss in the aging retina. Relationship to lipofuscin accumulation and macular degeneration. Investigative Ophthalmology and Visual Science 30 (1989), pp. 1691-1699.
5. L. Feeney-Burns, E. S. Hilderbrand and S. Eldridge, Aging human RPE: morphometric analysis of macular, equatorial, and peripheral cells. Investigative Ophthalmology and Visual Science 25 (1984), pp. 195-200.
6. F. G. Holz, C. Bellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
7. F. G. Holz, C. Hellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.
7. A. von Rückmann, F. W. Fitzke and A. C. Bird, Fundus autofluorescence in age-related macular disease imaged with a laser scanning ophthalmoscope. Investigative Ophthalmology and Visual Science 38 (1997), pp. 478-486.
9. F. G. Holz, C. Hellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
10. Sparrow J R, Fishkin N, Zhou J, Cai B, Jang Y P, Krane S, Itagaki Y, Nakanishi K. A2E, a byproduct of the visual cycle. Vision Res. 2003 December; 43(28):2983-90
11. Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401
12. Motani A, Wang Z, Conn M, Siegler K, Zhang Y, Liu Q, Johnstone S. Xu H, Thibault S, Wang Y, Fan P, Connors R, Le H, Xu G, Walker N, Shan B, Coward P. Identification and characterization of a non-retinoid ligand for retinol-binding protein 4 which lowers serum retinol-binding protein 4 levels in vivo. J Biol Chem. 2009 Mar. 20; 284(12): 7673-80.
13. Berni R, Formelli F. In vitro interaction of fenretinide with plasma retinol-binding protein and its functional consequences. FEBS Lett. 1992 Aug. 10; 308(1):43-5.
14. Schaffer E M, Ritter S J, Smith J E. N-(4-hydroxyphenyl) retinamide(fenretinide) induces retinol-binding protein secretion from liver and accumulation in the kidneys in rats. J Nutr. 1993 September; 123(9):1497-503
15. Adams W R, Smith J E, Green M H. Effects of N-(4-hydroxyphenyl)retinamide on vitamin A metabolism in rats. Proc Soc Exp Biol Med. 1995 February; 208(2):178-85.
16. Puduvalli V K, Saito Y, Xu R, Kouraklis G P, Levin V A, Kyritsis A P. Fenretinide activates caspases and induces apoptosis in gliomas. Clin Cancer Res. 1999 August; 5(8): 2230-5
17. Holmes W F, Soprano D R, Soprano K J. Synthetic retinoids as inducers of apoptosis in ovarian carcinoma cell lines. J Cell Physiol. 2004 June; 199(3):317-29

18. Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17
19. Fontana J A, Rishi A K. Classical and novel retinoids: their targets in cancer therapy. Leukemia. 2002 April; 16(4):463-72
20. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
21. Fontana J A, Rishi A K. Classical and novel retinoids: their targets in cancer therapy. Leukemia. 2002 April; 16(4):463-72
22. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
23. Sabichi A L, Xu H, Fischer S, Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13
24. Clifford J L, Menter D G, Wang M, Lotan R, Lippman S M. Retinoid receptor-dependent and -independent effects of N-(4-hydroxyphenyl)retinamide in F9 embryonal carcinoma cells. Cancer Res. 1999 Jan. 1; 59(1):14-8.
25. Gollapalli D R, Rando R R. The specific binding of retinoic acid to RPE65 and approaches to the treatment of macular degeneration. Proc Natl Acad Sci USA. 2004 Jul. 6; 101(27):10030-5
26. Maiti P, Kong J, Kim S R, Sparrow J R, Allikmets R, Rando R R. Small molecule RPE65 antagonists limit the visual cycle and prevent lipofuscin formation. Biochemistry. 2006 Jan. 24; 45(3):852-60
27. Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci USA. 2003 Apr. 15; 100(8):4742-7
28. Monaco H L, Rizzi M, Coda A. Structure of a complex of two plasma proteins: transthyretin and retinol-binding protein. Science. 1995 May 19; 268(5213):1039-41.
29. Bonanni B, Lazzeroni M, Veronesi U. Synthetic retinoid fenretinide in breast cancer chemoprevention. Expert Rev Anticancer Ther. 2007 April; 7(4):423-32.
30. Sunness J S, Margalit E, Srikumaran D, Applegate C A, Tian Y, Perry D, Hawkins B S, Bressler N M. The long-term natural history of geographic atrophy from age-related macular degeneration: enlargement of atrophy and implications for interventional clinical trials. Ophthalmology. 2007 February; 114(2):271-7.
31. Glickman J F et al. A comparison of ALPHAScreen, TR-FRET, and TRF as assay methods for FXR nuclear receptors. J. Biomol. Screening 2002; 7:3-10
32. Fujimura T et al. Unique properties of coactivator recruitment caused by differential binding of FK614, an anti-diabetic agent, to PPARgamma. Biol. Pharm. Bull. 2006; 29:423-429
33. Zhou G et al. Nuclear receptors have distinct affinities fo coactivators: characterization by FRET. Mol. Endocrinol. 1998; 12:1594-1605
34. Cogan U, Kopelman M, Mokady S, Shinitzky M. Binding affinities of retinol and related compounds to retinol binding proteins. Eur J Biochem. 1976 May 17; 65(1):71-8.
35. Decensi A, Torrisi R, Polizzi A, Gesi R, Brezzo V, Rolando M, Rondanina G, Orengo M A, Formelli F, Costa A. Effect of the synthetic retinoid fenretinide on dark adaptation and the ocular surface. J Natl Cancer Inst. 1994 Jan. 19; 86(2):105-10.
36. Conley B, O'Shaughnessy J, Prindiville S, Lawrence J, Chow C, Jones E, Merino M J, Kaiser-Kupfer M I, Caruso R C, Podgor M, Goldspiel B, Venzon D, Danforth D, Wu S, Noone M, Goldstein J, Cowan K H, Zujewski J. Pilot trial of the safety, tolerability, and retinoid levels of N-(4-hydroxyphenyl) retinamide in combination with tamoxifen in patients at high risk for developing invasive breast cancer. J Clin Oncol. 2000 January; 18(2):275-83.
37. Fain G L, Lisman J E. Photoreceptor degeneration in vitamin A deprivation and retinitis pigmentosa: the equivalent light hypothesis. Exp Eye Res. 1993 September; 57(3): 335-40.
38. Makimura H, Wei J, Dolan-Looby S E, Ricchiuti V, Grinspoon S. Retinol-Binding Protein Levels are Increased in Association with Gonadotropin Levels in Healthy Women. Metabolism. 2009 April; 58(4): 479-487.
39. Yang Q, Graham T E, Mody N, Preitner F, Peroni O D, Zabolotny J M, Kotani K, Quadro L, Kahn B B. Serum retinol binding protein 4 contributes to insulin resistance in obesity and type 2 diabetes. Nature. 2005 Jul. 21; 436 (7049):356-62.
40. Kim S R, Jang Y P, Jockusch S, Fishkin N E, Turro N J, Sparrow J R. The all-trans-retinal dimer series of lipofuscin pigments in retinal pigment epithelial cells in a recessive Stargardt disease model. PNAS. Dec. 4, 2007, Vol. 104, No. 49, 19273-8.
41. Wu Y, Fishkin N E, Pande A, Pande J, Sparrow R J. Novel Lipofuscin Bisretinoids Prominent in Human Retina and in a Model of Recessive Stargardt Disease. Journal of Biological Chemistry. Jul. 24, 2009, Vol. 284, No. 30, 20155-20166.
42. F. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.

What is claimed is:

1. A method for treating a disease characterized by excessive lipofuscin accumulation in the retina in mammal afflicted therewith, comprising administering to the mammal an effective amount of a compound having the structure:

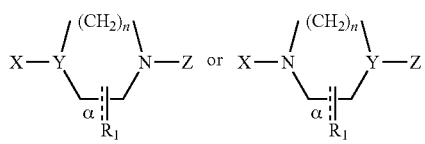

wherein
n=2 or 3;
$R_1$ is absent or present and when present, is $CH_3$ or O;
α is absent or present,
  wherein when α present, then $R_1$ is O, and when α is absent, then $R_1$ is $CH_3$;

X is
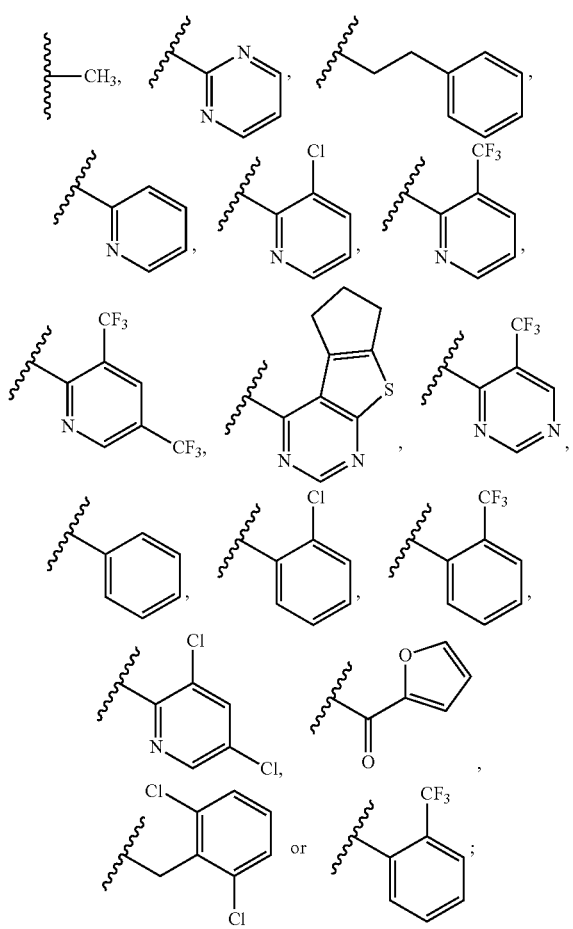
Y is N or C;
Z is
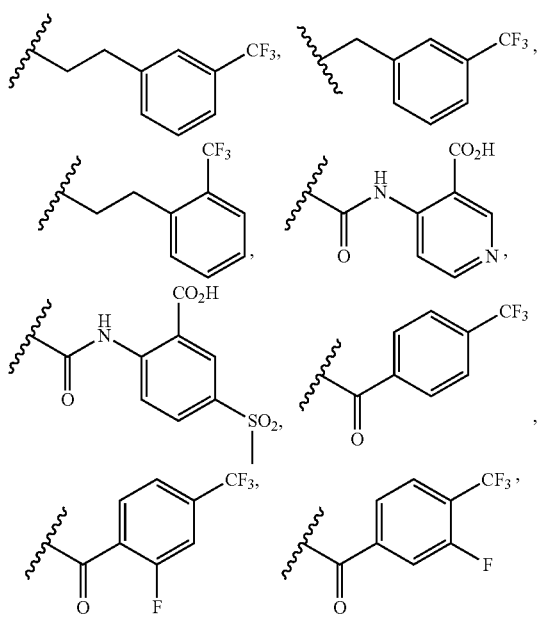
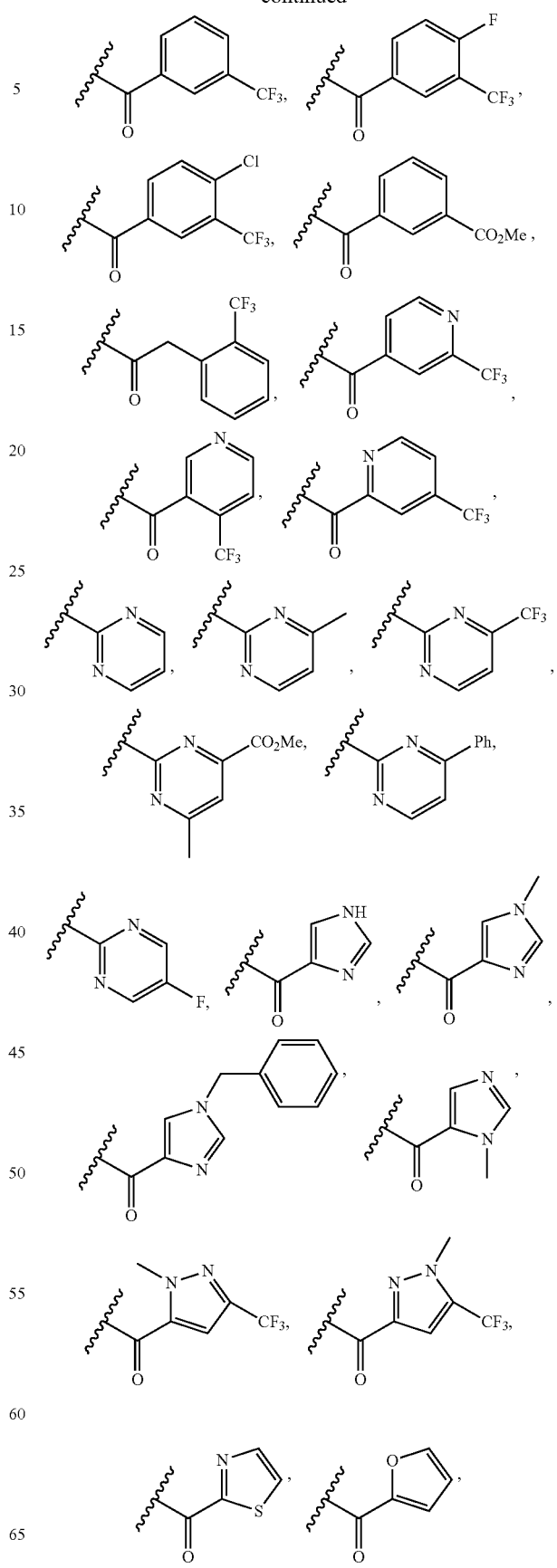

-continued
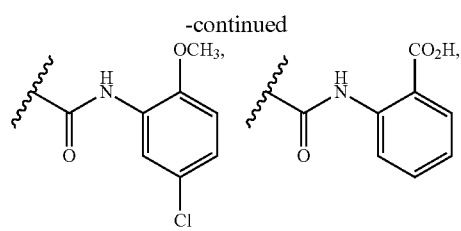
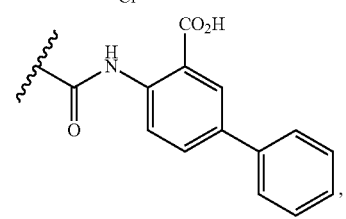
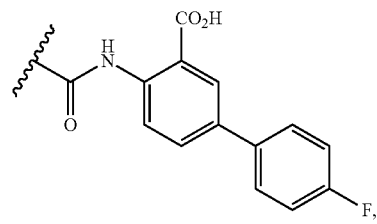
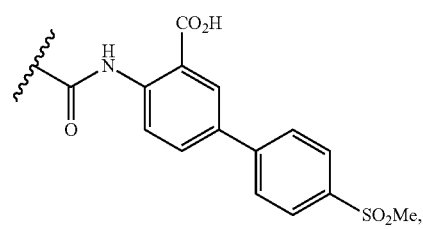
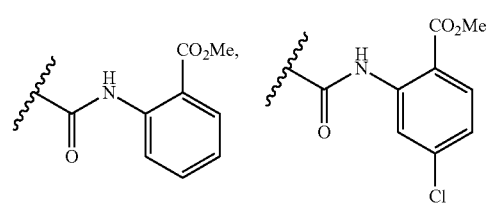
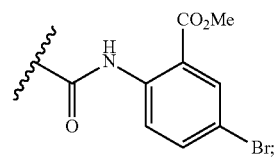 [SMILES: *C(=O)Nc1ccc(Br)cc1C(=O)OC]
and
when n=2, R₁ is absent, X is
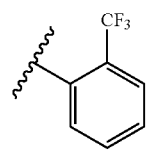 [SMILES: *c1ccccc1C(F)(F)F]
and Y is C,
then Z is other than
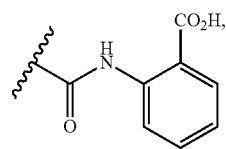
or a pharmaceutically acceptable salt thereof.
2. The method of claim 1, wherein the compound has the structure
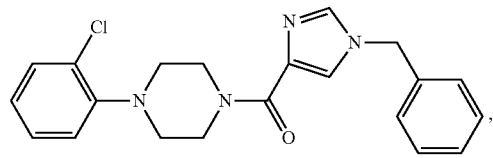
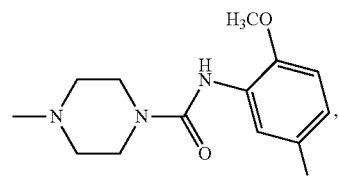
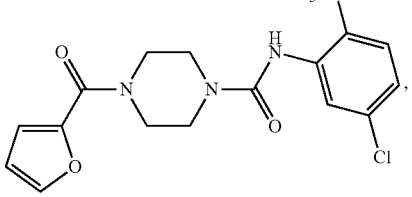
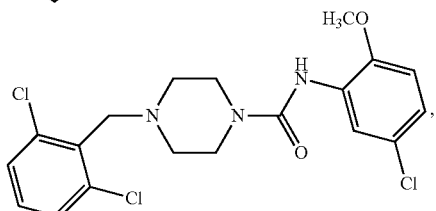
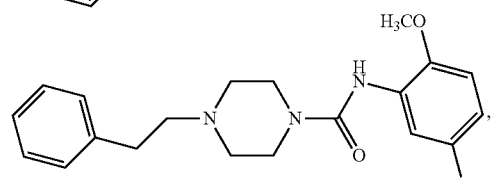
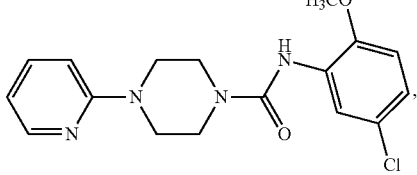

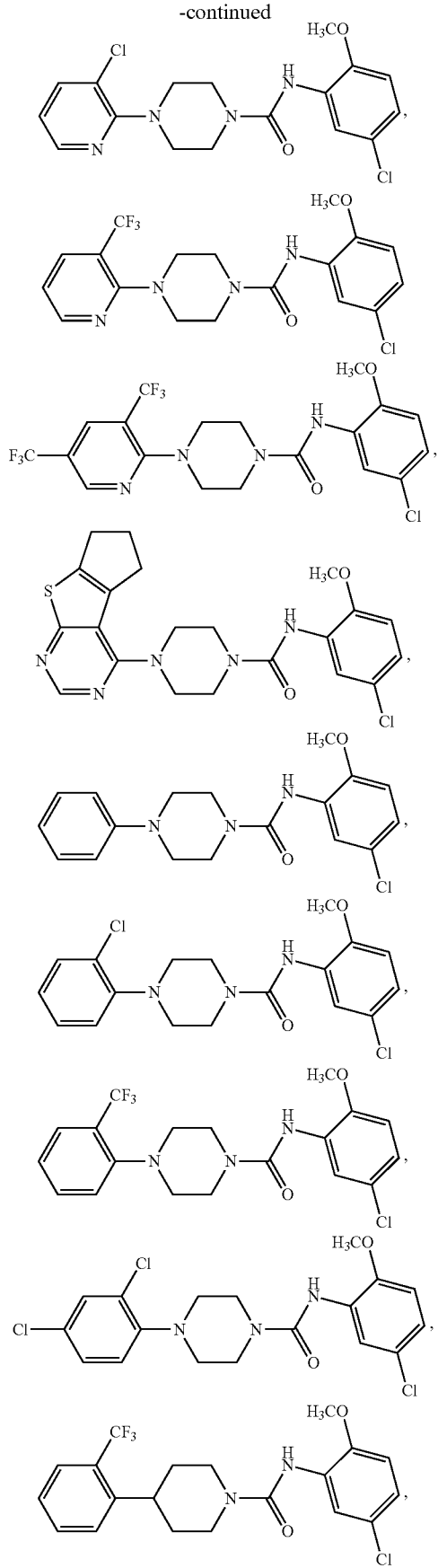
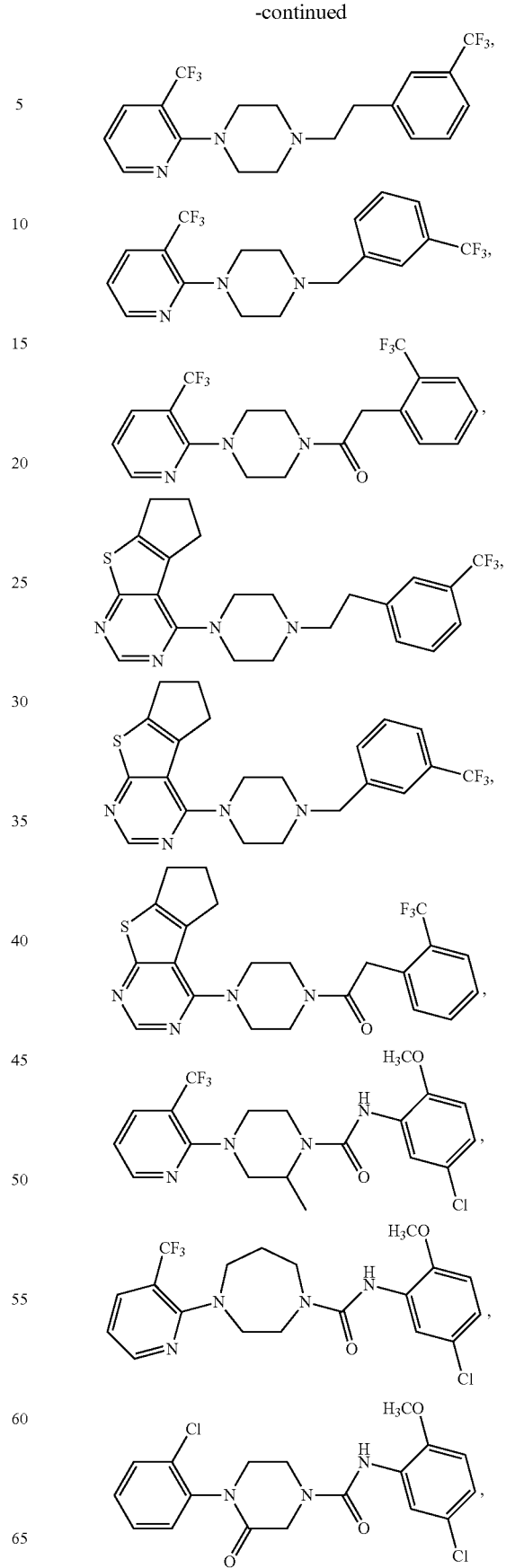

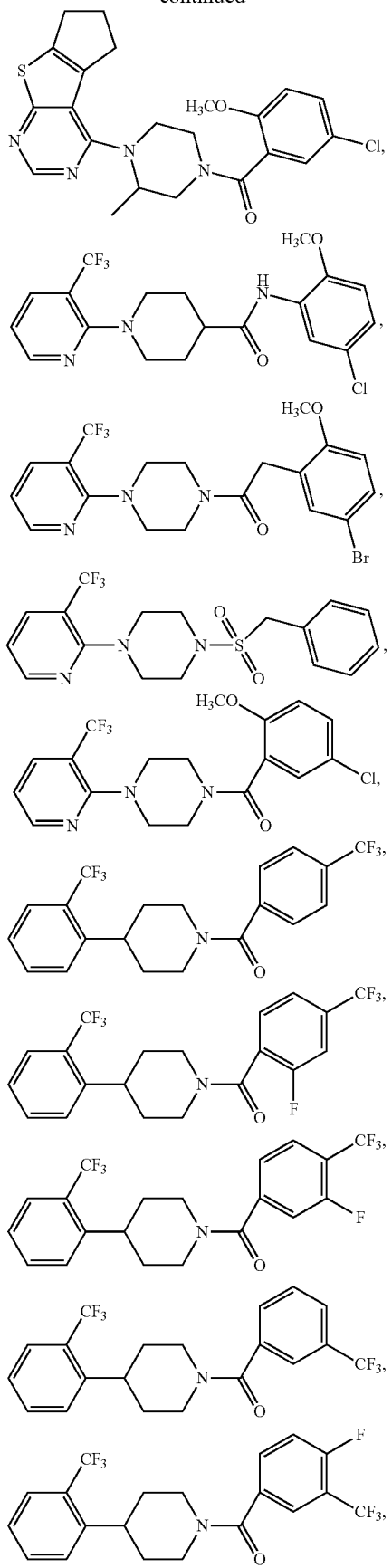
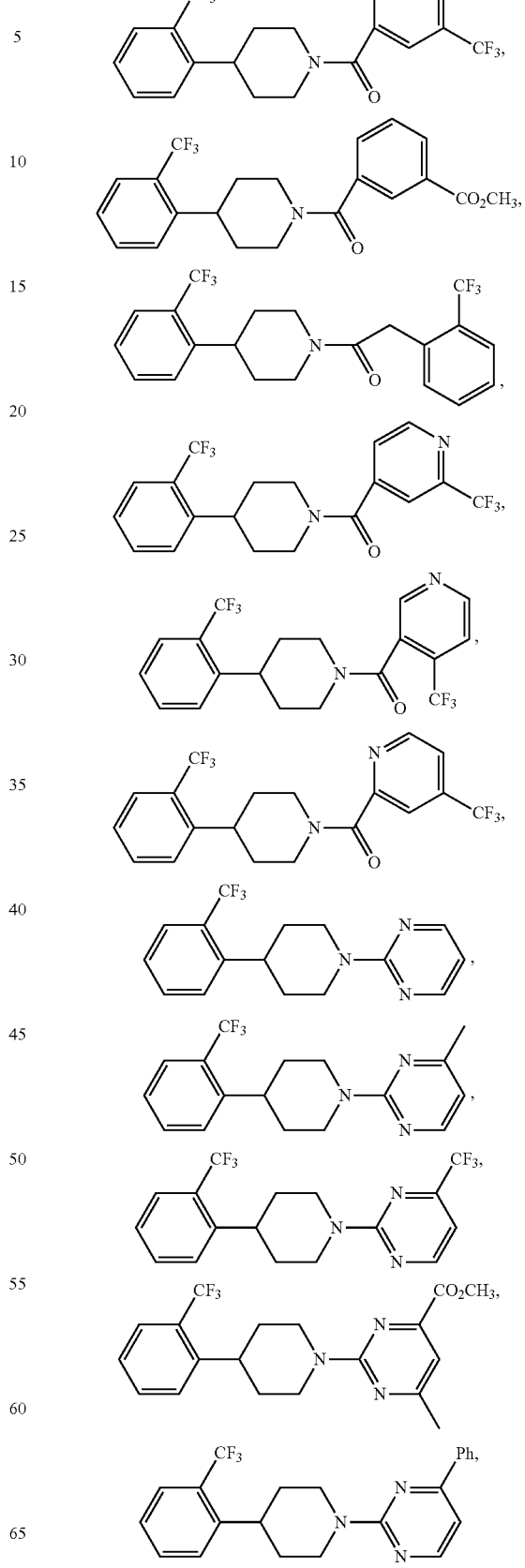

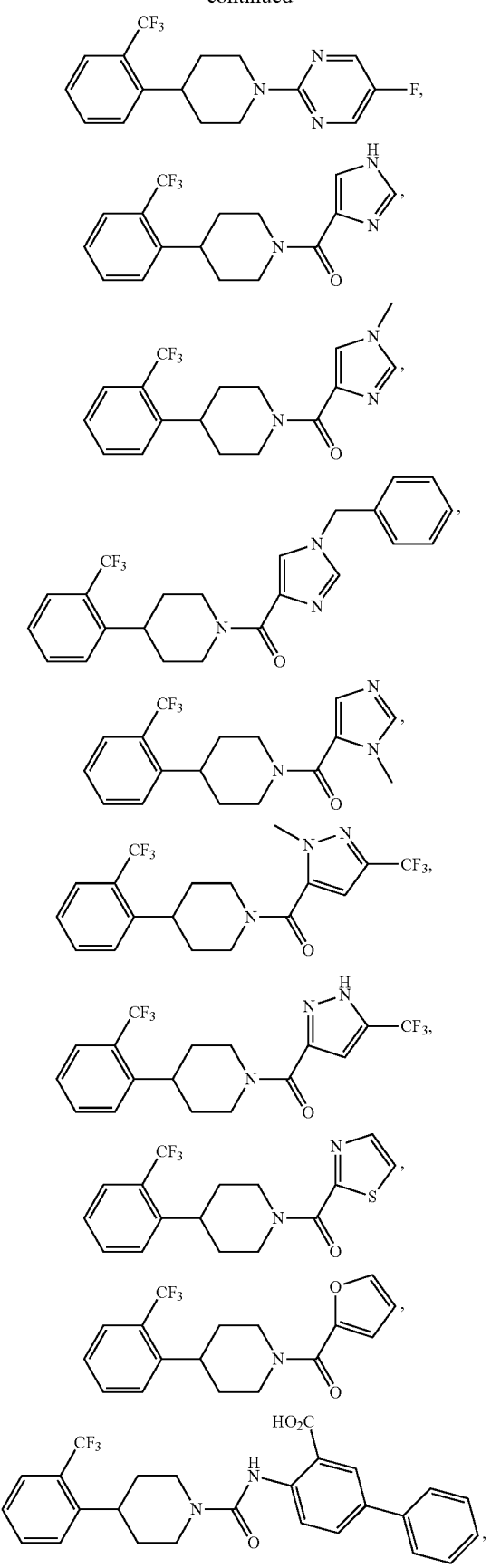
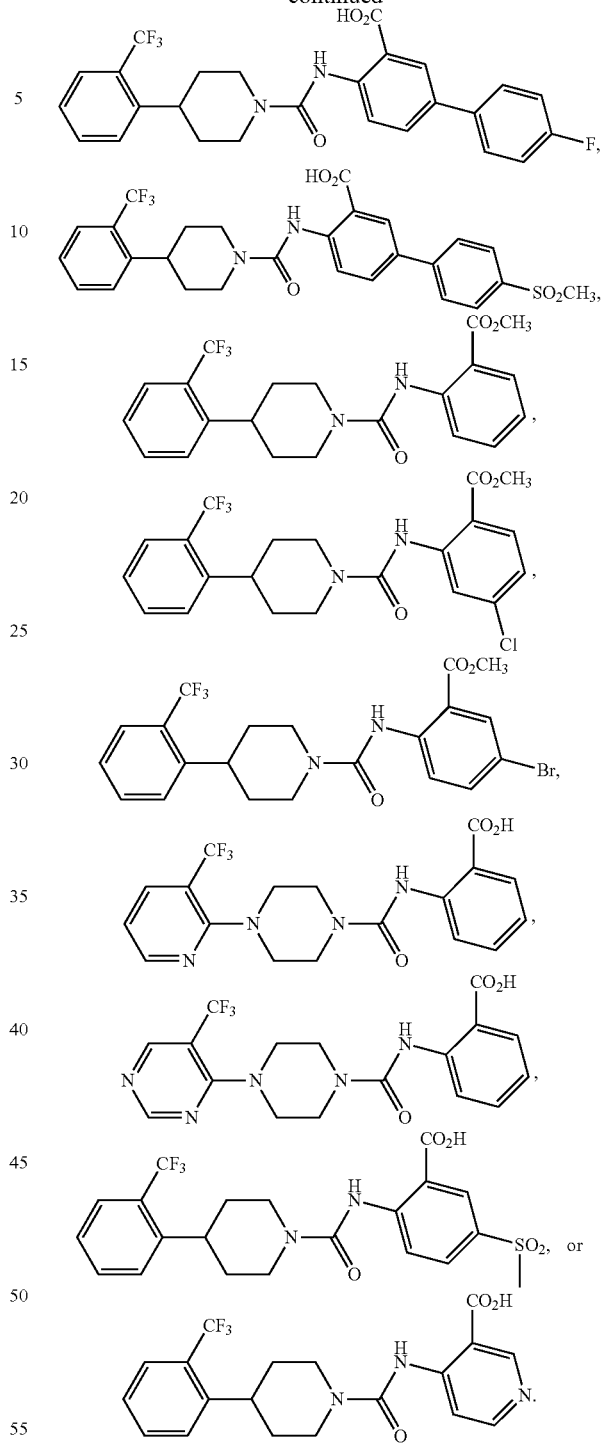

or a pharmaceutically acceptable salt thereof.

3. The method of claim 1 wherein the disease is further characterized by bisretinoid-mediated macular degeneration.

4. The method of claim 3, wherein the amount of the compound is effective to lower the serum concentration of RBP4 in the mammal.

5. The method of claim 3, wherein the amount of the compound is effective to lower the retinal concentration of a bisretinoid in lipofuscin in the mammal.

6. The method of claim 3, wherein the bisretinoid is A2E.

7. The method of claim 3, wherein the bisretinoid is isoA2E.

8. The method of claim 3, wherein the bisretinoid is A2-DHP-PE.

9. The method of claim 3, wherein the bisretinoid is atRAL di-PE.

10. The method of claim 3, wherein the disease characterized by excessive lipofuscin accumulation in the retina is Age-Related Macular Degeneration.

11. The method of claim 3, wherein the disease characterized by excessive lipofuscin accumulation in the retina is dry (atrophic) Age-Related Macular Degeneration.

12. The method of claim 3, wherein the disease characterized by excessive lipofuscin accumulation in the retina is Stargardt Disease.

13. The method of claim 3, wherein the disease characterized by excessive lipofuscin accumulation in the retina is Best disease.

14. The method of claim 3, wherein the disease characterized by excessive lipofuscin accumulation in the retina is adult vitelliform maculopathy.

15. The method of claim 3, wherein the disease characterized by excessive lipofuscin accumulation in the retina is Stargardt-like macular dystrophy.

* * * * *